US010595972B2

(12) United States Patent
Fisker

(10) Patent No.: US 10,595,972 B2
(45) Date of Patent: Mar. 24, 2020

(54) METHOD AND USER INTERFACE FOR USE IN MANUFACTURING MULTI-SHADED DENTAL RESTORATIONS

(71) Applicant: 3Shape A/S, Copenhagen K (DK)

(72) Inventor: Rune Fisker, Virum (DK)

(73) Assignee: 3Shape A/S, Copenhagen K (DK)

( * ) Notice: Subject to any disclaimer, the term of this patent is extended or adjusted under 35 U.S.C. 154(b) by 233 days.

(21) Appl. No.: 15/027,815

(22) PCT Filed: Oct. 2, 2014

(86) PCT No.: PCT/EP2014/071194
§ 371 (c)(1),
(2) Date: Apr. 7, 2016

(87) PCT Pub. No.: WO2015/052080
PCT Pub. Date: Apr. 16, 2015

(65) Prior Publication Data
US 2016/0242881 A1    Aug. 25, 2016

(30) Foreign Application Priority Data
Oct. 7, 2013    (DK) .................................. 2013 70561

(51) Int. Cl.
*A61C 13/08*    (2006.01)
*A61C 13/00*    (2006.01)

(52) U.S. Cl.
CPC ........ *A61C 13/082* (2013.01); *A61C 13/0004* (2013.01); *A61C 13/0022* (2013.01)

(58) Field of Classification Search
CPC ........................... A61C 13/0004; A61C 13/082
See application file for complete search history.

(56) References Cited

U.S. PATENT DOCUMENTS

2010/0021859 A1    1/2010    Kopelman
2011/0125304 A1    5/2011    Schneider et al.

FOREIGN PATENT DOCUMENTS

| EP | 1 252 867 A1 | 10/2002 |
| EP | 2 016 922 A2 | 1/2009 |
| EP | 2 325 771 A2 | 5/2011 |
| WO | WO 02/09612 A1 | 2/2002 |

OTHER PUBLICATIONS

International Search Report (PCT/ISA/210) dated Nov. 26, 2014, by the European Patent Office as the International Searching Authority for International Application No. PCT/EP2014/071194.
Written Opinion (PCT/ISA/237) dated Nov. 26, 2014, by the European Patent Office as the International Searching Authority for International Application No. PCT/EP2014/071194.
Search Report dated May 20, 2014, by the Danish Patent Office for Application No. PA 2013 70561.

*Primary Examiner* — Douglas King
(74) *Attorney, Agent, or Firm* — Buchanan Ingersoll & Rooney PC

(57) ABSTRACT

Disclosed is a method, a system, and a user interface for determining a preferred relative arrangement of digital restoration designs and digital representations of multi-shaded milling blocks for use when manufacturing dental restorations from multi-shaded milling blocks. A preferred first relative arrangement of a first digital restoration design and a digital representation of a first multi-shaded milling block is determined, and therefrom a preferred second relative arrangement of a second digital restoration design and a digital representation of a second multi-shaded milling block is determined.

22 Claims, 13 Drawing Sheets

111  110

113  112

METHOD AND USER INTERFACE FOR USE IN MANUFACTURING MULTI-SHADED DENTAL RESTORATIONS

FIELD OF THE INVENTION

The invention relates to a method, a system and a user interface for determining preferred relative arrangements of digital restoration designs and digital representations of multi-shaded milling blocks from which milling blocks dental restorations are to be manufactured.

BACKGROUND OF THE INVENTION

In CAD/CAM based techniques for the design and manufacture of dental restorations a digital representation of the dental restoration, herein referred to as a digital restoration design, is generated using Computer Aided Design (CAD) software. Based on the generated digital restoration design the physical restoration is subsequently manufactured using Computer Aided Manufacturing (CAM) equipment.

A dental restoration can be manufactured from a milling block of a dental material, such as Zirconia, by removing milling block material until the remaining part of the milling block has the desired shape of the dental restoration. When manufacturing a dental restoration from a milling block using CAD/CAM techniques, the portions of the milling block which are to be removed can be derived from a digital representation of the multi-shaded milling block and a digital restoration design by means of an electronic data processing device, such as the microprocessor of a computer. In a given relative arrangement of the digital restoration design and the digital representation of the milling block, the former define a sub-volume of the latter such that when the milling block material located outside this sub-volume is removed, e.g. by milling, the dental restoration is formed from the milling block.

The shade of natural teeth usually varies over the tooth surface and dental restorations manufactured from single-shaded milling blocks often cannot mimic the correct aesthetic properties of natural teeth. Multi-shaded dental restorations manufactured from multi-shaded milling blocks can provide a more correct aesthetic appearance than what can be obtained from single-shaded milling blocks. The multi-shaded milling block has a distribution of shades, e.g. a number of parallel layers of different shades, such that the shade profile of the manufactured dental restoration depends on the location of the sub-volume of the milling block from which the dental restoration is manufactured.

Several multi-shaded milling blocks are commercially available ranging from blocks with parallel layers of different shades to milling blocks where the shade distribution is designed to mimic the dentine of a tooth (e.g. VITABLOCS RealLife by Vident) or milling blocks that are crown shaped (e.g. priticrown milling blocks from Pritidenta GmbH).

In CAD/CAM based techniques, the digital representation of the multi-shaded milling block comprises shade data describing the shade distribution of the multi-shaded block. In order to obtain a preferred aesthetic appearance of the dental restoration, the digital restoration design and the digital representation of the multi-shaded milling block must be arranged according to a preferred relative arrangement in which geometry data of the digital restoration design and the shade data are aligned to provide the preferred aesthetic appearance for the manufactured dental restoration. For a milling block with a number of parallel layers of different shades it may e.g. be preferred to manufacture the dental restoration such that the incisal edge or occlusal surface of the dental restoration is substantially parallel with these layers.

US20110125304 describes a dental CAD/CAM system that can generate and display simulated images of the aesthetic properties of a single dental restoration using design data representing the dental restoration, data representing the surface of the dental restoration, data representing the volume of a milling block, and data representing aesthetic properties of the milling block.

However, it remains a problem to provide a method, a system and a user interface for determining preferred relative arrangements of a plurality of digital restoration designs and digital representations of multi-shaded milling blocks where symmetric aesthetic properties are obtained for left-right sets of dental restorations.

SUMMARY

It is an object of the invention to provide a method, a system and a user interface for use in manufacturing two or more multi-shaded dental restorations having mirror symmetric shading with respect to a symmetry plane of the patient. The dental restorations can be those of a left-right set, such as dental restorations for the left and right upper central incisors, which often provides the most aesthetic appearance when manufactured with symmetric shade profiles.

It is an object of the invention to provide a method, a system and a user interface for use in manufacturing two or more multi-shaded dental restorations with shade profiles that mimics natural tooth enamel of the corresponding teeth.

It is an object of the invention to provide a method, a system and a user interface for determining a preferred relative arrangement of digital restoration designs and digital representations of multi-shaded milling blocks for use when manufacturing dental restorations from multi-shaded milling blocks.

It is an object of the invention to provide a method, a system and a user interface for arranging digital restoration designs and digital representations of multi-shaded milling blocks relative to each other.

It is an object of the invention to provide a method, a system and a user interface for creating a set of shaded digital restoration designs for manufacturing a set of dental restorations for a patient's set of teeth.

It is an object of the invention to provide a method, a system and a user interface for quickly and precisely determining the preferred relative arrangement of the digital restoration designs and digital representations of multi-shaded milling blocks for a left-right set of dental restorations.

It is an object of the invention to provide a method, a system and a user interface for a computer assisted arrangement of digital restoration designs and digital representations of multi-shaded milling blocks such that symmetric shade profiles for equivalent restorations in a left-right set of dental restorations can be obtained easily, quickly and with high precision.

It is an object of the invention to provide a method, a system and a user interface for manufacturing multi-shaded dental restorations from multi-shaded milling blocks, where the shade profile of a manufactured dental restoration depends on the relative arrangement of the digital restoration design and the digital representation of the multi-shaded milling block Disclosed is a method for determining a preferred relative arrangement of digital restoration designs and digital representations of multi-shaded milling blocks for use when manufacturing dental restorations from multi-shaded milling blocks, the method comprising:

obtaining digital representations of at least a first and a second multi-shaded milling block, where each digital representation comprises shade data describing the shade distribution of the multi-shaded milling block;

obtaining at least a first and a second digital restoration design; and determining a preferred first relative arrangement of the first digital restoration design and the digital representation of the first multi-shaded milling block, and determining therefrom a preferred second relative arrangement of the second digital restoration design and the digital representation of the second multi-shaded milling block.

Multi-shaded first and second dental restorations can be manufactured from the first and second multi-shaded milling blocks based on the first and second digital restoration designs, where the shade profile of a manufactured dental restorations depend on the relative arrangement of the digital restoration design and the digital representation of the multi-shaded milling block.

In some embodiments, the preferred second relative arrangement is performed at least partly by computer implemented algorithms executed by an electronic data processing device.

In the context of the present invention, the phase "shade" may refer to the color and translucency of the tooth, where the color may be described by hue (i.e. the actual color of the tooth), value (i.e. the brightness of the tooth) and chroma (i.e. the saturation/intensity of the color).

In the context of the present invention, the phase "milling block" refers to a piece of dental material from which the dental restoration can be manufactured by e.g. milling, laser cutting, or any other suitable method for removal of material (depending on the material and demands for e.g. precision and production time).

In the context of the present invention, the phrase "multi-shaded milling block" refers to a milling block comprising dental material of at least two different shades, such as a milling block with layers of material with different shades or material with a shade gradient throughout the milling block.

In the context of the present invention, the phrase multi-shaded milling block refers to a single coherent piece, where the single coherent piece comprises dental material of at least two different shades. One example of such a multi-shaded milling block is a coherent block having three layers of dental material with different shades. Another example is a portion of a larger disc-shaped blank where the portion forms a single coherent piece of dental material with at least two different shades.

In the context of the present invention, the phase "dental restoration" is used in relation to the item that is formed when the removal of material from the milling block of dental material is complete while the phase "milling block" refers to the complete milling block and all its shapes during the process of removing milling block material until the removal of material is complete and the remaining part has the shape of the dental restoration.

In the context of the present invention, the phase "for use when manufacturing dental restorations from multi-shaded milling blocks" refers both to the situation where the dental restorations subsequently are manufactured and to the situation where a demonstration of the expected visual appearance of the dental restorations is to be presented e.g. to the patient or the operator. The invention can e.g. also be used for determining which milling blocks are most adequate in order to obtain the most aesthetic result.

The relative arrangement of a digital restoration design and a digital representation of a multi-shaded milling block can be described by the relative position and the relative orientation of the two. I.e. determining the preferred relative arrangement may comprise determining both the relative position and orientation of the digital restoration design and the digital representation of the multi-shaded milling block.

In cases where the preferred second relative arrangement is determined by mirroring the preferred first relative arrangement, the relative position of the second digital restoration design and the digital representation of second multi-shaded milling block can be identical to the relative position of the first digital restoration design and the digital representation of first multi-shaded milling block, while the relative orientations may be symmetric across the mirror plane.

When the shade distribution of a multi-shaded milling block differs along one axis only (henceforth referred to as the z-axis) the digital restoration design can be displaced in a perpendicular plane (i.e. the x-y plane) without changing the shade profile of the manufactured dental restoration. Further, a rotation of the digital restoration design around the z-axis does not change the shade profile. In contrast a displacement along the z-axis or a rotation around an axis which has a component in the x-y plane will result in a change in the shade profile of the manufactured dental restoration.

A "digital restoration design" may also be referred to as a "Virtual dental restoration".

In some embodiments determining the preferred second relative arrangement comprises copying the preferred first relative arrangement to the preferred second relative arrangement. The preferred second relative arrangement is then identical to the preferred first relative arrangement, such that the relative arrangement of the second digital restoration design and the digital representation of the second multi-shaded milling block is identical to the relative arrangement of the first digital restoration design and the digital representation of the first multi-shaded milling block in the preferred first relative arrangement. In cases where the first and second digital restoration designs and the first and second multi-shaded milling blocks are identical, copying the preferred relative arrangement then provides that the manufactured first and second dental restorations are identical.

This may be advantageous when the preferred first relative arrangement and the shade distribution of identical first and second multi-shaded milling blocks provides a shade profile of the manufactured first dental restoration (and hence of the manufactured second dental restoration) which has variations which are parallel to the patient's occlusal plane and/or the incisal edge/occlusal surface of the dental restoration.

In some embodiments determining the preferred second relative arrangement comprises mirroring the preferred first relative arrangement to the preferred second relative arrangement. The relative arrangement of the second digital restoration design and the digital representation of the second multi-shaded milling block in the preferred second relative arrangement is then mirror symmetric to the relative arrangement of the first digital restoration design and the digital representation of the first multi-shaded milling block in the preferred first relative arrangement.

In many cases, the first and second dental restorations of a left-right set are shaped to be symmetric across a symmetry plane of the patient, such as the patient's saggital plane. When the restorations are manufactured from mirror symmetric milling blocks, it is then advantageous to have mirror symmetric preferred relative arrangements since this provides that the shade profile of the first digital restoration design is mirrored to the second digital restoration design such that a highly aesthetic result is obtained. The shade distribution of the first and second milling blocks does evidently not need to have variations which are parallel to the incisal or occlusal edge of the dental restorations manufactured therefrom in order for this approach to be advantageous.

When the preferred first relative arrangement is mirrored to the preferred second relative arrangement, the second digital restoration design is arranged in relation to the shade data of the digital representations of the second multi-shaded milling block in such a manner that the second digital restoration design is aligned with the shade data according to the alignment of the first digital restoration design and the shade data of the digital representation of first multi-shaded milling block.

In some embodiments determining the preferred first relative arrangement comprises adjusting the relative arrangement of the first digital restoration design and the digital representation of the first multi-shaded milling block while inspecting a simulated image.

In some embodiments, the simulated image is at least partly created by mapping the shade data of the digital representation of the first multi-shaded milling block onto the first digital restoration design. The shade data are then mapped onto the digital representation according to the current first relative arrangement of the first digital restoration design and the digital representation of the first multi-shaded milling block, such that the simulated image represents the shade profile and the shape of a dental restoration manufactured from the current sub-volume of the milling block. When the first relative arrangement is adjusted, the sub-volume changes and with it often the shade profile of the manufactured dental restoration. The change is seen in the simulated image and can be updated concurrently with the changes in the relative arrangement such that the operator can determine the preferred first relative arrangement based on the inspection of the simulated image.

The simulated image can be visualized to an operator in a user interface presented on a visual display unit such as a computer screen, where the simulated image is updated for every change made to the relative arrangement of the first digital restoration design and the digital representation of the first multi-shaded milling block. Using e.g. a pointing tool, such as a computer mouse, the operator can move the first digital restoration design and the digital representation of the first multi-shaded milling block relative to each other until a preferred first relative arrangement is determined in which the shade profile of the manufactured first dental restoration will have a desired aesthetical appearance. Often the shade profile of the restoration is chosen by the operator based on her or his personal preference.

In some embodiments, the simulated image is at least partly created by superimposing the digital representations of the first and second milling blocks on the first and second digital restoration designs.

The simulated image can be visualized to an operator in a user interface presented on a visual display unit such as a computer screen. Using e.g. a pointing tool, such as a computer mouse, the operator can move the digital representation of the first multi-shaded milling block relative to the first digital restoration design until a preferred first relative arrangement is determined in which the shade profile of the manufactured first dental restoration will have a desired aesthetical appearance. In embodiments where the preferred second relative arrangement is determined for every change of the preferred first relative arrangement, the arrangement of the digital representation of the second multi-shaded milling block relative to the second digital restoration design and/or relative to the digital representation of the first multi-shaded milling block may be automatically updated for every change in the preferred first relative arrangement. Instead of moving the digital representation of the first multi-shaded milling block relative to the first digital restoration design, the first digital restoration design can be moved relative to the digital representation of the first multi-shaded milling block whereby the same results can be obtained.

In some embodiments the shade distributions of the multi-shaded milling blocks comprise a number of layers of different shades, and the shade data of the digital representations of the multi-shaded milling blocks comprises corresponding virtual layers.

In some embodiments, the digital representations of the first and second multi-shaded milling blocks comprise both shade data describing the shade distribution and shape data describing the shape of the multi-shaded milling block. The digital restoration designs and the digital representations of the milling blocks can then be visualized together in a visual display unit in which their relative arrangement can be manipulated using e.g. a pointing tool such as a computer mouse. The digital representations of the multi-shaded milling blocks may be represented by CAD blocks comprising data describing the shape of the multi-shaded milling blocks.

In some embodiments, the digital representation of the first and/or second milling block is a digital 3D representation describing the 3D nature of the milling block such that there is a direct correspondence with the physical multi-shaded milling blocks.

In some embodiments, the digital representations of the milling blocks are visualized as semitransparent virtual blocks showing interfaces between layers of different shades.

This has the advantage that the operator can estimate the adequateness of a current relative arrangement of the digital restoration designs and the digital representations of the milling blocks by inspecting visualizations of these on a computer screen.

In some embodiments, the preferred first relative arrangement is such that the incisal edge of the first digital restoration design is aligned with a layer of the digital representation of the first multi-shaded milling block.

In some embodiments, the digital restoration designs are placed such that they copy the planned relative arrangement of the dental restorations in the patient's mouth. The digital restoration designs may be visualized together with parts of a digital representation of the patient's existing teeth with the digital restoration designs placed anatomically correct relative to these parts, i.e. according to the planned placement of the manufactured dental restorations in the patient's set of teeth. When the set of teeth and the shape of the dental restorations of a left-right set are such that the incisal edge or occlusal surface of the dental restorations are aligned, an aesthetic correct result can often be obtained if the shade profiles of the dental restorations also are aligned. This can be achieved by aligning the digital representations of the multi-shaded milling blocks, such as by aligning their edges, surfaces or the shade data of the digital representations.

In some embodiments determining the preferred second relative arrangement comprises aligning the digital representation of the second multi-shaded milling block with the digital representation of the first multi-shaded milling block.

This is advantageous when the first and second digital restoration designs are visualized together, e.g. visualized superimposed in a simulated image, with the relative arrangement of the digital restoration designs copying the planned relative arrangement of the dental restorations in the patient's mouth. With the digital representation of the first multi-shaded milling block arranged according to the preferred first relative arrangement, the aligning of the digital representation of the second multi-shaded milling block with the digital representation of the first multi-shaded milling block provides that the digital representation of the second multi-shaded milling block and the second digital restoration design are arranged according to the preferred second relative arrangement. The relative arrangement of the first digital restoration design and the digital representation of the first multi-shaded milling block can hence be directly mirrored or copied to the relative arrangement of the second digital restoration design and the digital representation of the second multi-shaded milling block A computer program product or a user interface configured for implementing the method may be utilizing computer implemented alignment algorithms for this alignment such that the alignment is performed automatically. In some embodiments, the user interface comprises a virtual tool which when activated provides that such alignment algorithms are executed to provide that the digital representation of the second multi-shaded milling block is aligned with the digital representation of the first multi-shaded milling block.

In some embodiments aligning the digital representation of the second multi-shaded milling block with the digital representation of the first multi-shaded milling block is based on the shade data of the digital representations.

Aligning the digital representations based on the shade data is advantageous e.g. when the first and second digital restoration designs are arranged according to their anatomical correct relationship since this allows an easy determining of the preferred second relative arrangement from the preferred first relative arrangement.

In some embodiments aligning the digital representation of the second multi-shaded milling block with the digital representation of the first multi-shaded milling block is based on the shape data of the digital representations, such as on an edge or a surface of the multi-shaded milling blocks.

Aligning the digital representations based on the shape data is advantageous e.g. when shade distributions of the first and second milling blocks are identical and the first and second digital restoration designs are arranged according to their anatomical correct relationship since this allows an easy determining of the preferred second relative arrangement.

On both cases, the preferred second relative arrangement can be such that it e.g. copies or mirrors the shade profile of the first digital restoration design to the second digital restoration design.

In some embodiments aligning the digital representation of the second multi-shaded milling block with the digital representation of the first multi-shaded milling block is based on an edge or a surface of the multi-shaded milling blocks.

In some embodiments, the determined preferred first and second relative arrangements are such that the manufactured first and second dental restorations have similar s-hade profiles at their incisal edges/occlusal surfaces.

In some embodiments, the determining of the second preferred relative arrangements comprises adjusting the relative arrangement of the second digital restoration design and the digital representation of the second multi-shaded milling block until the shade profile at the incisal edge/occlusal surface of the second digital restoration design is similar to the shade profile at the incisal edge/occlusal surface of the first digital restoration design in the determined preferred first relative arrangement.

For some patient's such similar shade profiles at the incisal edges/occlusal surfaces provide the most aesthetic configuration of the patient's set of teeth with the seated restorations. The similar shade profiles may be such that the portions of the dental restorations at the incisal edges/occlusal surfaces which have the same brightness/shade are of equivalent height.

In some embodiments, the first and second digital restoration designs are arranged relative to a digital 3D representation of the patient's existing teeth created e.g. by a 3D scanning of the patient's set of teeth.

In some embodiments, the 3D scan is an intra-oral scan of at least part of the patient's set of teeth, a scan of at least part of an impression of the patient's set of teeth, and/or a scan of at least part of a physical model of the patient's set of teeth. The 3D scan may be performed by means of focus scanning, laser light scanning, white light scanning, probe-scanning, X-ray scanning, and/or CT scanning.

In some embodiments, the digital representations of the first and second multi-shaded milling blocks are identical and represent identical multi-shaded milling blocks.

This may be advantageous when the dental restorations preferably have similar shade profiles. This is often the case when the first and second restorations are those of a left-right set of restorations.

In some embodiments, one of the digital representations of the first and second multi-shaded milling blocks relate to a left geometry multi-shaded milling block while the other relates to a right geometry multi-shaded milling block.

This may be advantageous when the dentist/operator choses that the shade profiles of the dental restorations are not parallel to the patient's occlusal plane. This may be the case when the shade profiles of the patient's existing teeth are not parallel to the patient's occlusal plane.

In some embodiments, the first and second multi-shaded milling blocks are separate milling blocks, such as separate single-restoration milling blocks or separate multi-restoration milling blocks.

In some embodiments, at least one of the digital representations of the multi-shaded milling blocks is a digital 3D representation describing the 3D shape and shade distribution of the corresponding milling block.

In the context of the present invention separate portions of a coherent disc shaped multi-shaded blank can also be considered to be separate milling blocks in which case the digital representations of the first and second multi-shaded milling blocks comprises shade data and geometry data describing the shade distribution and the shade of these separate portions, respectively.

Both the first and the second dental restoration can comprise several teeth such as in a bridge comprising crowns and one or more pontics. In cases where several neighboring teeth are being replaced, the first dental restoration may form some of these teeth and the second dental restoration the remaining teeth.

The multi-shaded milling blocks can be manufactured in various materials such as Zirconia or PMMA. Zirconia is often the choice when manufacturing the final dental restoration while PMMA often used for the manufacture of e.g. a try-in for evaluating the fit of the dental restoration.

The invention is not limited to cases where preferred arrangements between two digital restoration designs and two digital representations of multi-shaded milling blocks is to be determined, but can equally be applied to cases with three or more dental restorations are to be manufactured from three or more milling blocks.

In some embodiments, the preferred relative arrangement for two digital restoration designs and digital representations of two multi-shaded milling blocks is determined.

In some embodiments, obtaining the digital representations of at least a first and a second multi-shaded milling block comprises loading these digital representations into an electronic data processing device, such as the microprocessor.

In some embodiments, obtaining at least a first and a second digital restoration design comprises loading these digital restoration designs into an electronic data processing device.

In some embodiments, determining a preferred first relative arrangement of the first digital restoration design and the digital representation of the first multi-shaded milling block comprises executing computer implemented algorithms using an electronic data processing device, where the algorithms are configured for determining the preferred first relative arrangement.

In some embodiments, determining a preferred second relative arrangement of second first digital restoration design and the digital representation of the second multi-shaded milling block comprises executing computer implemented algorithms using an electronic data processing device, where the algorithms are configured for determining the preferred second relative arrangement from the preferred first relative arrangement.

In some embodiments, the first and second digital restoration designs relate to a left-right set of dental restorations.

In the context of the present invention, the phase "left-right set of restorations" refers to dental restorations which by nature have the similar shape and shade profile. For example the equivalent teeth of the lower left quadrant and lower right quadrant, such as the left and right mandibular cuspids, form a left-right set. The left-right set of dental restorations can also contain two or more dental restorations on each side of the patient's mouth. For example the left and right maxillary incisors can form a left-right set.

In some embodiments, the preferred second relative arrangement is chosen to be similar to the preferred first relative arrangement in such a manner that the digital restoration designs of a left-right set have the similar alignments with the shade data/distribution of the respective digital representations of multi-shaded milling blocks.

In some embodiments, the preferred second relative arrangement is determined after the preferred first relative arrangement. I.e. the preferred relative arrangement of the second digital restoration design and the digital representation of the second milling block is determined after the preferred relative arrangement of the first digital restoration design and the digital representation of the first milling block is determined. The relative arrangement of the second digital restoration design and the digital representation of the second multi-shaded milling block is hence not adjusted in response to every change in the relative arrangement of the first digital restoration design and the digital representation of the first multi-shaded milling block. Steps to determine the preferred second relative arrangement, e.g. by mirroring, are thus first initiated after the preferred first relative arrangement is determined.

This has the advantage that the operator can focus on determining the preferred first relative arrangement without being concerned or distracted by the preferred second relative arrangement, and that no computer calculation power is needed to simultaneously update the second relative arrangement for every change in the first relative arrangement. For example, when determining the preferred first relative arrangement using simulated images, a simulated image for the second dental restoration is not determined in response to every change in the relative arrangement of the first digital restoration design and the digital representation of the first multi-shaded milling block.

In some embodiments the preferred second relative arrangement and the preferred first relative arrangement are determined simultaneously. I.e. the preferred relative arrangement of the second digital restoration design and the digital representation of the second milling block is determined simultaneously with the preferred relative arrangement of the first digital restoration design and the digital representation of the first milling block. When determining the preferred first relative arrangement using a simulated image created e.g. by mapping shade data onto the first digital restoration design, a simulated image for the second dental restoration is then created in response to any change in the relative arrangement of the first digital restoration design and the digital representation of the first multi-shaded milling block.

This can be advantageous in embodiments where the shade data are mapped onto the digital restoration designs since the collective appearance of the first and second dental restorations can be evaluated for every change made in the arrangement of the first digital restoration design and the digital representation of the first multi-shaded milling block. But also in embodiments where digital representations of the multi-shaded milling blocks are visualized together with digital restoration designs this approach can be advantageous since this may automatically provide an impression of the collective appearance of the manufacture dental restorations.

In some embodiments, the preferred second relative arrangement is determined from the relative arrangement of the incisal edge/occlusal surface of the first digital restoration design and the opposing surface of the digital representation of the first multi-shaded milling block in the first preferred relative arrangement.

The incisal edge/occlusal surface of the second digital restoration design and the opposing surface of the digital representation of the second multi-shaded milling block can be arranged according to the relative arrangement of the incisal edge/occlusal surface of the first digital restoration design and the opposing surface of the digital representation of the first multi-shaded milling block.

This may be advantageous when the patient's existing teeth that will surround the dental restorations are asymmetric with e.g. incisal edges that are not aligned. The digital restoration designs can then be designed to at least partly compensate for the asymmetry by e.g. having offset incisal edges.

In some embodiments, determining the preferred second relative arrangement comprises providing an offset to the digital representation of the second multi-shaded milling block, such as an offset relative to the digital representation of the first multi-shaded milling block and/or relative to the first digital restoration design and/or relative to the second digital restoration design. The offset is preferably configured to at least partly compensate for an asymmetry in the digital restoration designs created for the patient's teeth and/or an asymmetry in the size and shape of the patient's existing teeth which will surround the manufactured restorations when these are seated in the patient's mouth. In cases where the first and second multi-shaded milling blocks are identical a matching of the offset of the digital representation of the second multi-shaded milling block with the offset in the planned placement of the first and second dental restorations can provide that the manufactured dental restorations have similar shade profiles at their incisal edges/occlusal surfaces.

In some embodiments, the determining of the preferred second relative arrangement is based on a measurement of the distance from the incisal/occlusal edge of the first digital restoration design to the opposing boundary of the digital representation of the first multi-shaded milling block.

Disclosed is a user interface for determining a preferred relative arrangement of digital restoration designs and digital representations of multi-shaded milling blocks for use when manufacturing dental restorations from multi-shaded milling blocks, where the user interface is configured for:
    obtaining digital representations of at least a first and a second multi-shaded milling block, where each digital representation comprises shade data describing the shade distribution of the multi-shaded milling block;
    obtaining at least a first and a second digital restoration design;
    visualizing at least the first digital restoration design and at least the shade data of the digital representation of the first multi-shaded milling block; and
    determining a preferred first relative arrangement of the first digital restoration design and the digital representation of the first multi-shaded milling block, and determining therefrom a preferred second relative arrangement of the second digital restoration design and the digital representation of the second multi-shaded milling block.

The shade profile of a manufactured dental restoration depends on the relative arrangement of the digital restoration design and the digital representation of the multi-shaded milling block, such that by changing the relative arrangement, the shade profile of the dental restoration can change.

In some embodiments, geometry data of the digital representation of the first multi-shaded milling block describing the shape of the milling block are visualized together with the shade data and the first digital restoration design. This may e.g. be the case when the digital representations of the first and second multi-shaded milling blocks are superimposed on the first and second digital restoration designs forming a simulated image.

In some embodiments, the user interface comprises a virtual tool which when activated determines the preferred second relative arrangement from the preferred first relative arrangement, e.g. by copying or mirroring the preferred first relative arrangement to the preferred second relative arrangement. The virtual tool can be realized as a virtual push button visualized in the user interface.

In some embodiments, the digital representations of the first and second multi-shaded milling blocks comprises the shade data describing the shade of the multi-shaded milling blocks and the user interface is configured for visualizing the digital restoration designs and the digital representations of the multi-shaded milling blocks together. The virtual tool can then be configured for aligning the digital representations of the multi-shaded milling blocks when activated. When the digital restoration designs are arranged according to the planned relative arrangement of the manufactured dental restorations in the patient's mouth, the aligning of the digital representations of the multi-shaded milling blocks can provide that the preferred second relative arrangement is determined by copying or mirroring the preferred first relative arrangement.

In some embodiments, the shade data of the digital representation of the first multi-shaded milling block is mapped onto the first digital restoration design to create a simulated image of the resulting appearance of the manufactured dental restoration. The user interface is then preferably configured for visualizing the simulated image allowing an operator to determine the preferred first relative arrangement by inspecting changes in the simulated image resulting from changes in the relative arrangement of the first digital restoration design and the digital representation of the first multi-shaded milling block and/or its shade data. This can e.g. be achieved by a virtual movement tool of the user interface allowing the operator to move the first digital restoration design and digital representation of the first multi-shaded milling block relative to each other. The simulated image may only visualize the digital representation of the milling block as the shade data mapped onto the digital restoration design without showing the shape of the milling block. In that case it may be advantageous that the virtual movement tool is configured for moving the first digital restoration design relative to the digital representation of the first multi-shaded milling block and thus relative to the shade data. The virtual movement tool is then capable of grabbing and moving the first digital restoration design in the user interface while the digital representation of the first multi-shaded milling block is held at a constant position.

The preferred first relative arrangement can be identified as the relative arrangement at which the operator is satisfied with the appearance of the simulated image. Another virtual tool of the user interface can be configured for determining the preferred second relative arrangement by e.g. copying or mirroring the preferred first relative arrangement when it is activated.

The user interface can be implemented using a computer system where the user interface is visualized using a computer screen showing the different components of the user interface, such a data entry fields and virtual push buttons configured for performing one or more steps of a method according to an embodiment of the invention. Data entry means such as a computer mouse and a computer keyboard can be connected to the computer system and used for entering data into the user interface and for making selections by e.g. pressing said virtual push buttons using the computer mouse.

In some embodiments, the user interface is configured for allowing an operator to carry out a method according to an embodiment of the invention. Preferably, at least one of the steps of obtaining digital representations of the multi-shaded milling blocks, obtaining digital restoration designs, determining the preferred first relative arrangement, and determining therefrom the preferred second relative arrangement can be performed by the operator using said user interface.

In some embodiments, the steps of the method are performed sequentially and the user interface can be configured for sequentially providing a visually representation of the steps to the operator such that the sequence of the user interface matches that of the method. In some embodiments, the user interface is configured for simultaneously providing a visually representation of two or more of the steps to the operator.

Disclosed is a method for arranging digital restoration designs and digital representations of multi-shaded milling blocks relative to each other, the method comprising:
  obtaining digital representations of at least a first and a second multi-shaded milling block, where each digital representation comprises shade data describing the shade distribution of the multi-shaded milling block;
  obtaining at least a first and a second digital restoration design; and
  arranging the digital restoration designs and the digital representations of the multi-shaded milling blocks relative to each other, where the relative arrangement of the first digital restoration design and the digital representation of the first multi-shaded milling block is taken into account when arranging the second digital restoration design and the digital representation of the second multi-shaded milling block relative to each other.

Disclosed is a method for creating a set of shaded digital restoration designs for manufacturing a set of dental restorations for a patient's set of teeth, where the method comprises:
  obtaining digital representations of at least a first and a second multi-shaded milling block, where each digital representation comprises shade data describing the shade distribution of the multi-shaded milling block;
  obtaining at least a first and a second digital restoration design;
  determining a preferred first relative arrangement of the first digital restoration design and the digital representation of the first multi-shaded milling block and projecting the shade data of the first multi-shaded milling block onto the first digital restoration design based on this preferred first relative arrangement; and
  arranging the second digital restoration design and the digital representation of the second multi-shaded milling block relative to each other taking into account the preferred first relative arrangement, and projecting the shade data of the second multi-shaded milling block onto the second digital restoration design.

Disclosed is a method for determining a preferred relative arrangement of digital restoration designs and digital representations of multi-shaded milling blocks for use when manufacturing dental restorations from multi-shaded milling blocks, the method comprising:
  loading digital representations of at least a first and a second multi-shaded milling block into an electronic data processing device, where each digital representation comprises shade data describing the shade distribution of the multi-shaded milling block;
  loading at least a first and a second digital restoration design into said electronic data processing device;
  executing computer implemented algorithms using said electronic data processing device, where the algorithms are configured for determining a preferred first relative arrangement of the first digital restoration design and the digital representation of the first multi-shaded milling block; and
  executing computer implemented algorithms using said electronic data processing device, where the algorithms are configured for determining a preferred second relative arrangement of the second digital restoration design and the digital representation of the second multi-shaded milling block from the preferred first relative arrangement.

Disclosed is a method for manufacturing multi-shaded dental restorations from multi-shaded milling blocks, where the shade profile of a manufactured dental restoration depends on the relative arrangement of the digital restoration design and the digital representation of the multi-shaded milling block, the method comprising:
  obtaining digital representations of at least a first and a second multi-shaded milling block, where each digital representation comprises shade data describing the shade distribution of the multi-shaded milling block;
  obtaining at least a first and a second digital restoration design;
  determining a preferred first relative arrangement of the first digital restoration design and the digital representation of the first multi-shaded milling block and determining therefrom a preferred second relative arrangement of the second digital restoration design and the digital representation of the second multi-shaded milling block;
  determining which portions of the milling blocks which are located outside sub-volumes of the milling blocks defined by the digital restoration designs in their preferred relative arrangements; and
  manufacturing the dental restorations from the multi-shaded milling blocks by removal of the portions located outside the sub-volumes.

Furthermore, the invention relates to a computer program product comprising program code for causing an electronic data processing device to perform the method according to any of the embodiments, when said program code is executed by the electronic data processing device.

Furthermore, the invention relates to a computer program product comprising a computer-readable medium having stored there on the program code.

In some embodiments, the computer program product comprises algorithms for automatically aligning the digital representation of the second multi-shaded milling block with the digital representation of the first multi-shaded milling block. This can be advantageous in embodiments where the digital restoration designs and the digital representations of the multi-shaded milling blocks are arranged according to their planned relative arrangement in the patient's mouth.

Disclosed is a non-transitory computer readable medium storing thereon a computer program, where said computer program is configured for causing computer-assisted determining of preferred relative arrangements of digital restoration designs and digital representations of multi-shaded milling blocks wherein the preferred relative arrangements are determined using the method according to any of the embodiments.

Disclosed is a system for determining a preferred relative arrangement of digital restoration designs and digital representations of multi-shaded milling blocks for use when manufacturing dental restorations from multi-shaded milling blocks, the system comprising a non-transitory computer readable medium having one or more computer instructions stored thereon, where said computer instructions comprises instructions for carrying out a method of:
  obtaining digital representations of at least a first and a second multi-shaded milling block, where each digital representation comprises shade data describing the shade distribution of the multi-shaded milling block;
  obtaining at least a first and a second digital restoration design; and determining a preferred first relative arrangement of the first digital restoration design and the digital representation of the first multi-shaded milling block, and determining therefrom a preferred second relative arrangement of the second digital restoration design and the digital representation of the second multi-shaded milling block.

The present invention relates to different aspects including the method, computer program product, user interface and system described above and in the following, and corresponding methods, computer program products, user interfaces and systems, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

FIG. 1 shows examples of milling blocks of dental material from which dental restorations can be formed by a subtractive process where excess material is removed.

Figure 1A:
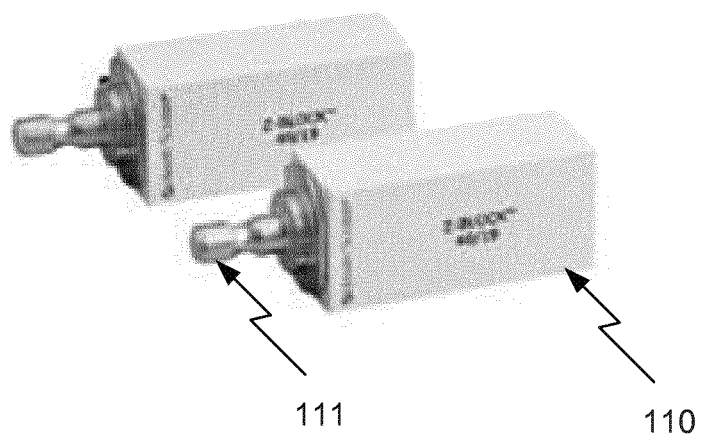
FIGS. 1A and 1B show examples of milling blocks

FIG. 1A shows two Zirconia milling blocks 110 with pins 111 for arranging the milling blocks in a milling machine.

Figure 1B:
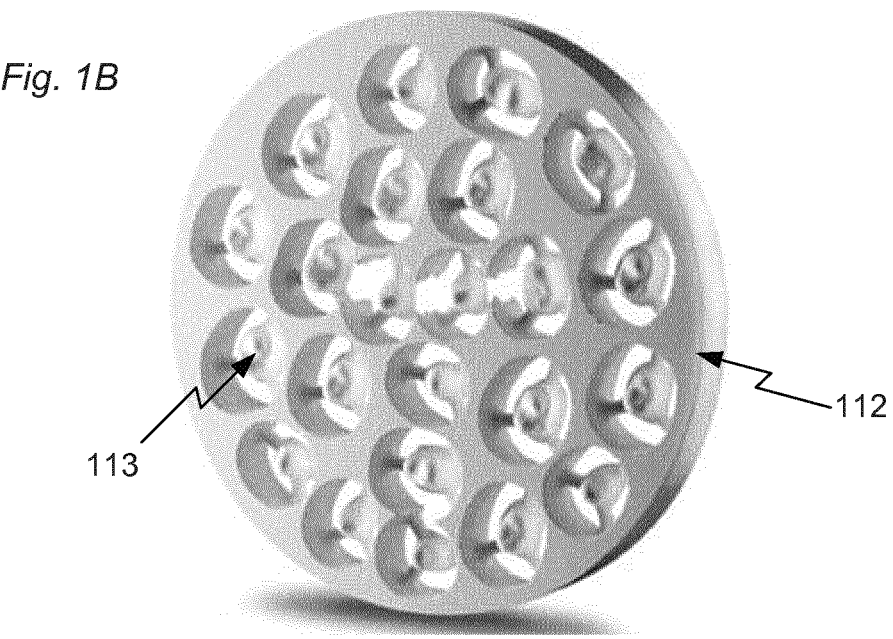

FIG. 1B shows a milling block in the shape of a blank 112 in which a number of single-crown dental restorations 113 have been formed by milling away blank material.

FIG. 2 illustrates the use of CAD/CAM for manufacturing dental restorations from milling blocks.

Figure 2A:
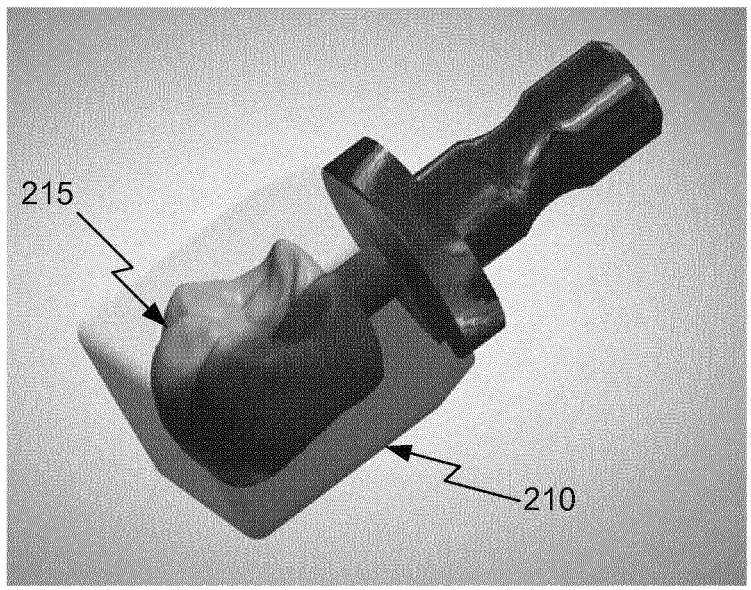
FIGS. 2A-2D illustrate the use of CAD/CAM for manufacturing dental restorations from milling blocks.
Figure 2B:
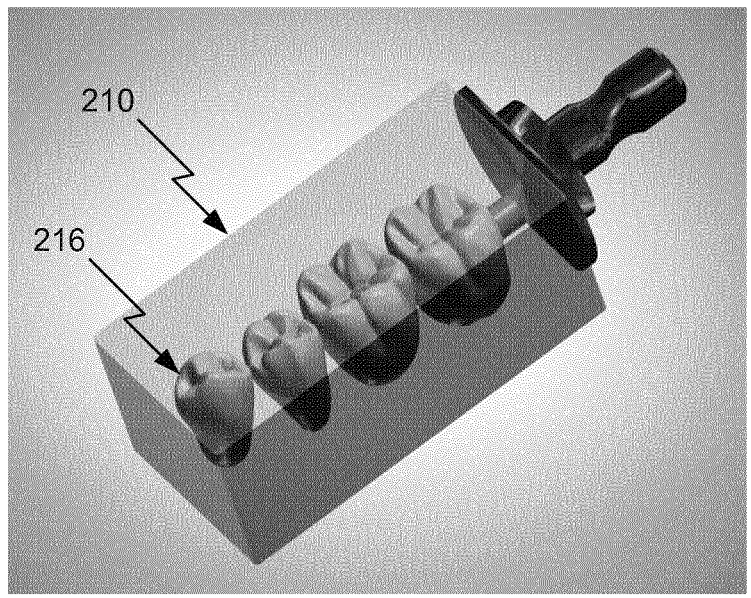

FIGS. 2A and 2B show screenshots of cases where a digital representation of a milling block 210 is visualized together with a digital restoration design 215, 216. The digital restoration design 215, 216 defines a sub-volume of the milling block from which the dental restoration is formed during a milling procedure. During the milling procedure, the material located outside the sub-volume is removed such that when the milling procedure is final the remaining material of the milling block forms the dental restoration. In both FIGS. 2A and 2B, the illustrated milling blocks 210 are single-shaded milling blocks. In FIG. 2A the digital restoration design 215 is for a single crown while in FIG. 2B it is for a bridge restoration having two pontics and two crowns for seating at prepared teeth or implant abutments in the patient's mouth.

Figure 2C:
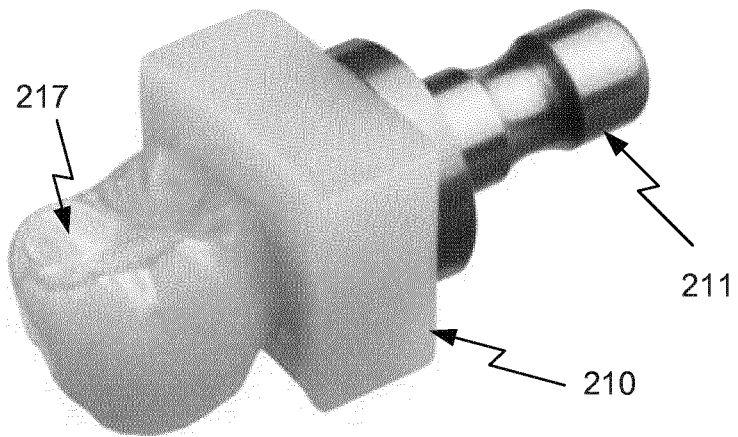

FIG. 2C shows a picture of a milling block where the milling process has been aborted before the dental restoration is fully formed. Where the material of the milling block located outside the sub-volume defined by the digital restoration design has been removed, the shape of the dental restoration 217 can be seen. At the section closest to the pin 211, material of the milling block 210 must be removed in order to complete the milling of the dental restoration.

Figure 2D:
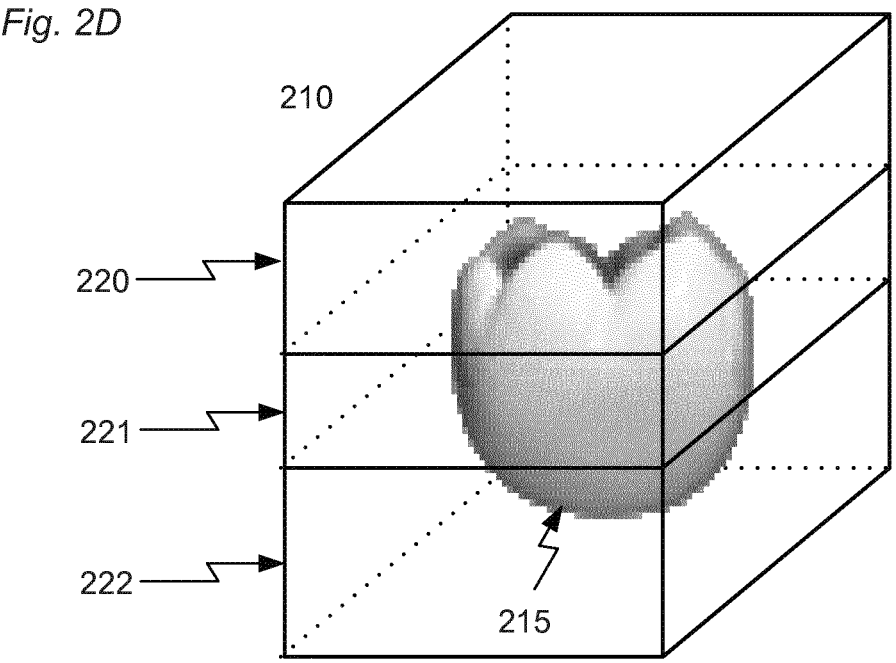

FIG. 2D shows a schematic of a relative arrangement of a digital restoration design 215 and a digital representation of a multi-shaded milling block 210. The milling block has three layers 220, 221, and 222 of materials with different shades, e.g. with the shade of the material of layer 220 being brighter than that of the material of layer 221, which again is brighter than the shade of the material of layer 222. The relative arrangement of the digital restoration design 215 and the digital representation of the multi-shaded milling block 210 determines the shade profile of the manufactured dental restoration, and with the illustrated arrangement the dental restoration will have a brighter shade at its occlusal surface that at the parts closer to the patient's gingiva. This can provide a more natural appearance of the dental restoration than what can be obtained with a single-shaded milling block.

Figure 3A:
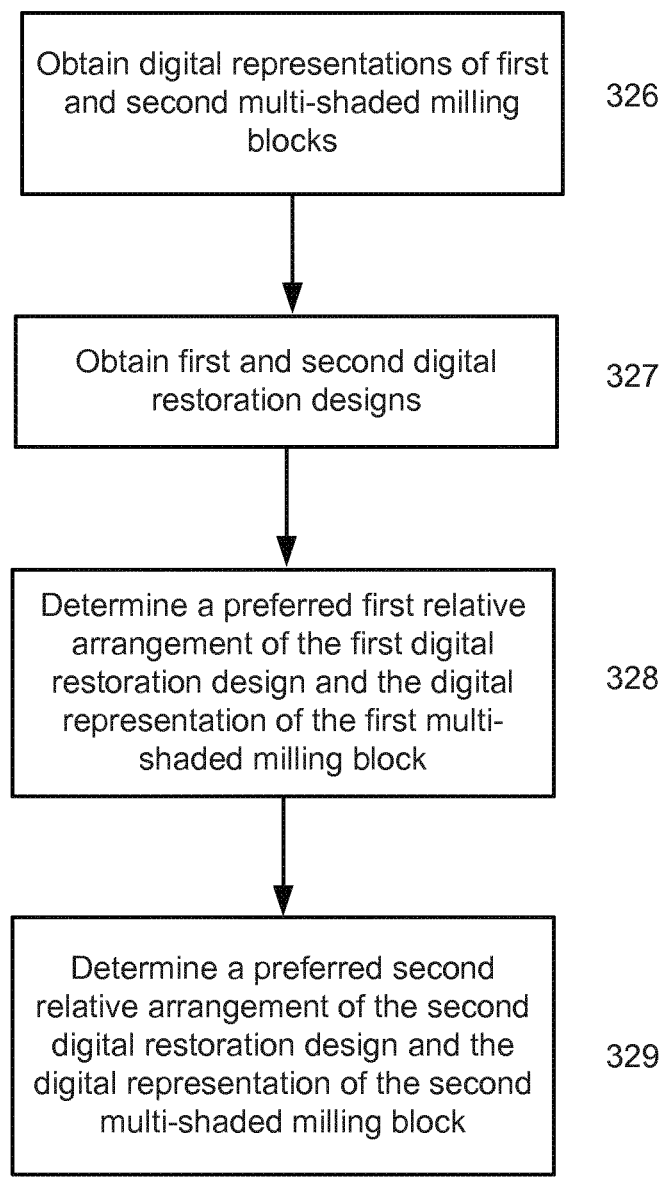
FIGS. 3A-3C show flowcharts for embodiments of the method.

FIG. 3 shows flowcharts for embodiments of the method according to the invention. FIG. 3A shows a flowchart 325 for a method for determining a preferred relative arrangement of digital restoration designs and digital representations of multi-shaded milling blocks for use when manufacturing dental restorations from multi-shaded milling blocks.

In step 326 digital representations of a first and a second multi-shaded milling block are obtained, where each digital representation comprises shade data describing the shade distribution of the multi-shaded milling block. This can be done by loading the digital representations into an electronic data processing device from a library comprising digital representations for a number of different milling blocks.

In step 327 a first and a second digital restoration design are obtained, based on which multi-shaded first and second dental restorations can be manufactured from the first and second multi-shaded milling blocks. The digital restoration designs can be obtained e.g. by designing these on a computer system using adequate CAD software such as the 3Shape Dental System software. Such software can be configured to allow an operator to select virtual library teeth from a tooth library or to design the dental restorations based on a digital representation of the patient's existing teeth. In cases where the dental restoration is intended to replace an existing tooth, the corresponding digital restoration design can be shaped based on a digital 3D representation of the patient's teeth obtained in a 3D scanning of the patient's existing teeth. In a left-right set of dental restorations, the second digital restoration design can be shaped by mirroring the first digital restoration design across a symmetry plane.

In step 328, a preferred first relative arrangement of the first digital restoration design and the digital representation of the first multi-shaded milling block is determined. This can be determined in different way such as those described in FIGS. 4 and 5.

In step 329, a preferred second relative arrangement of the second digital restoration design and the digital representation of the second multi-shaded milling block is determined from the preferred first relative arrangement. This is preferably performed at least in part by computer implemented algorithms executed by an electronic data processing device, such as the microprocessor of a computer system, based on choices entered by the operator e.g. whether the preferred second relative arrangement is to be determined by mirroring the preferred first relative arrangement.

Figure 3B:
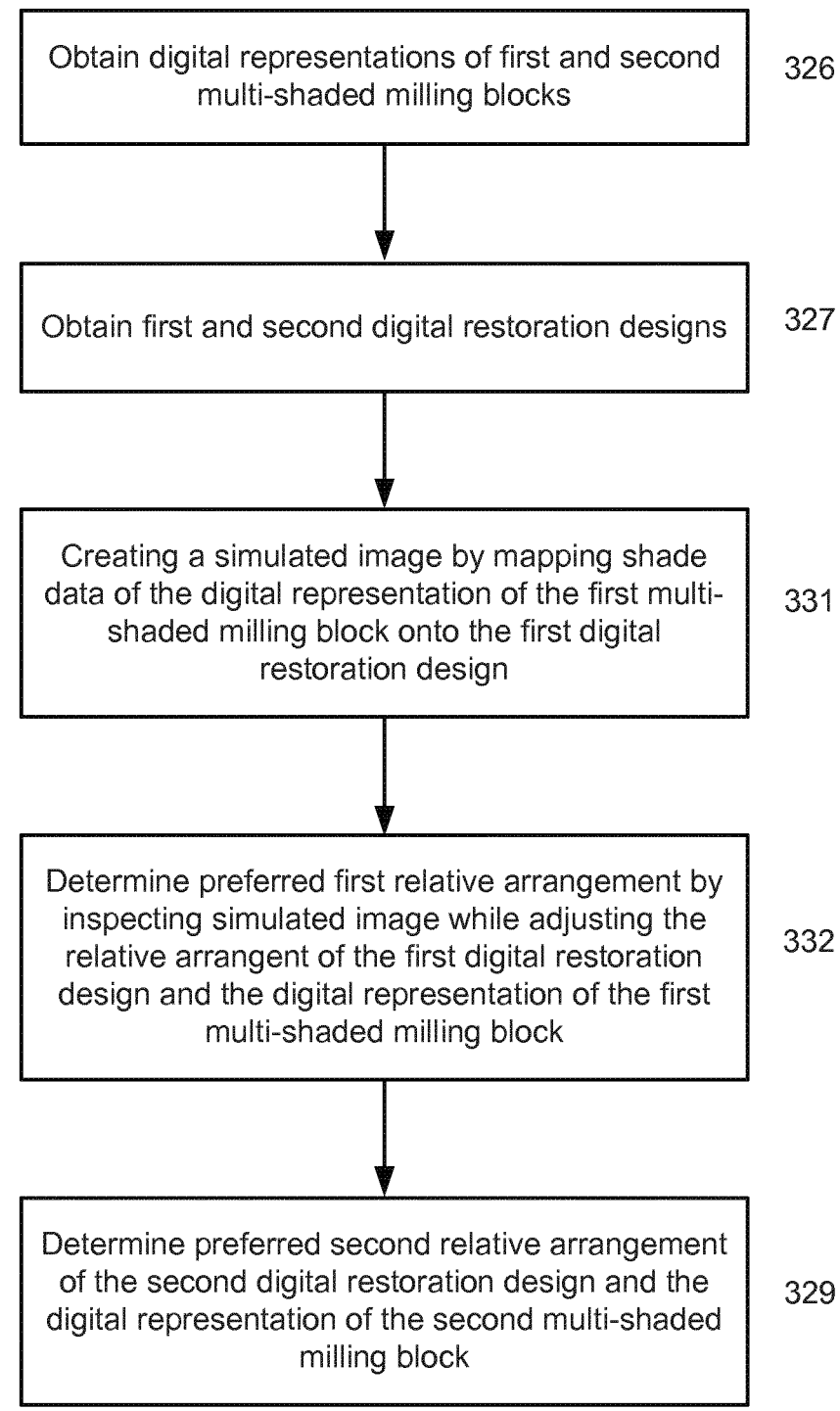

FIG. 3B shows a flowchart 330 for an embodiment where a simulated image created by mapping the shade data of the digital representation of the first multi-shaded milling block onto the first digital restoration design is used for determining the preferred first relative arrangement.

In steps 326 and 327 the digital representations of first and second multi-shaded milling blocks and the first and second digital restoration designs are obtained.

In step 331, the simulated image is created by mapping the shade data of the digital representation of the first multi-shaded milling block onto the first digital restoration design. The simulated image then illustrates the expected shape and shade profile of a dental restoration milled from the milling block with the current relative arrangement of the first digital restoration design and the digital representation of the first multi-shaded milling block. In this simulated image, the digital representation of the first multi-shaded milling block itself is not visualized.

A preferred first relative arrangement is determined in step 332 by adjusting the relative position of the first digital restoration design and the digital representation of the first multi-shaded milling block while inspecting the simulated image. This can be done using e.g. a pointing tool of a user interface where the position and orientation of the digital representation of the first multi-shaded milling block is held fixed. Moving the simulated image in the user interface then corresponds to moving the first digital restoration design relative to the digital representation of the first multi-shaded milling block.

In step 329 a preferred second relative arrangement of the second digital restoration design and the digital representation of the second multi-shaded milling block is determined from the preferred first relative arrangement. For a left-right set of dental restorations this can e.g. be done by mirroring the preferred first relative arrangement to the preferred second relative arrangement.

Figure 3C:
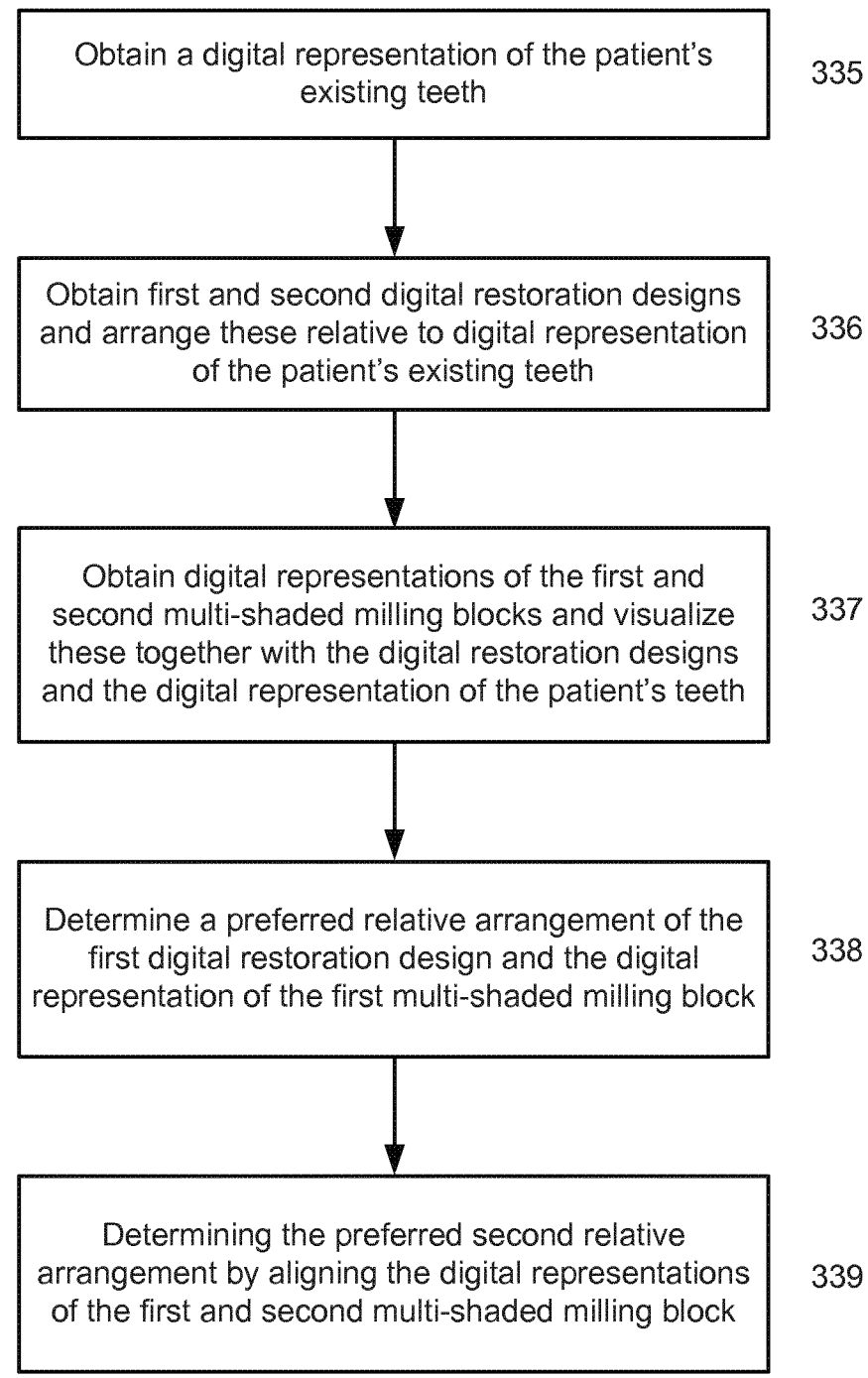

FIG. 3C shows a flowchart 334 for an embodiment wherein the digital representations of the first and second multi-shaded milling blocks comprises shape data describing the shape of the multi-shaded milling blocks, and the preferred second relative arrangement is determined by aligning the digital representations of the multi-shaded milling blocks.

In step 335, a digital representation of the patient's existing teeth is obtained e.g. by an intra-oral 3D scan of the patient's set of teeth in which case the digital representation of the patient's existing teeth is a digital 3D representation showing the 3D shape of the teeth.

In step 336 first and second digital restoration designs are obtained and arranged relative to the digital representation of the patient's existing teeth. The digital restoration designs can e.g. be arranged according to the planned placement of the manufactured dental restorations when these are seated at the patient's set of teeth. In step 337 digital representations of the first and second multi-shaded milling blocks are obtained and visualized together with the digital restoration designs in a simulated image created by superimposing the digital representations of the first and second milling blocks on the first and second digital restoration designs. The simulated image may also comprise the digital representation of the patient's set of teeth.

A preferred first relative arrangement of the first digital restoration design and the digital representation of the first multi-shaded milling block is then determined in step 338 by adjusting the relative arrangement of the first digital restoration design and the digital representation of the first multi-shaded milling block while inspecting the simulated image. This can be done by moving the digital representation of the first multi-shaded milling block using an appropriate virtual movement tool of a user interface in which the digital restoration designs and the milling blocks are visualized together with the digital representation of the patient's set of teeth.

In step 339, the preferred second target arrangement is determined by aligning the digital representation of the second multi-shaded milling block with the digital representation of the first multi-shaded milling block. In cases where the first and second multi-shaded milling blocks are identical, such that the corresponding digital representations are identical, the aligning can be based on the shade data and/or on an edge or surface of the digital representations of the multi-shaded milling blocks.

FIG. 4 shows a schematic presentation of an embodiment where the preferred second relative arrangements for two left-right sets of dental restorations are determined by aligning digital representations of the multi-shaded milling blocks.

Figure 4A:
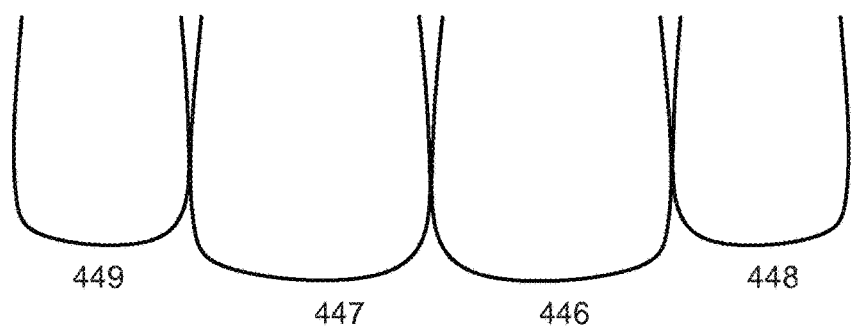
FIGS. 4A-4E show a schematic presentation of an embodiment.

FIG. 4A shows a schematic 445 (of the labial surfaces) of the two left-right sets of digital restoration designs, where one left-right set consists of the left and right upper central incisors 446, 447 and the other of the left and right upper lateral incisors 448, 449. The digital restoration designs are arranged according to the planned relative placement of the manufactured dental restorations when these are seated in the patient's mouth.

Figure 4B:
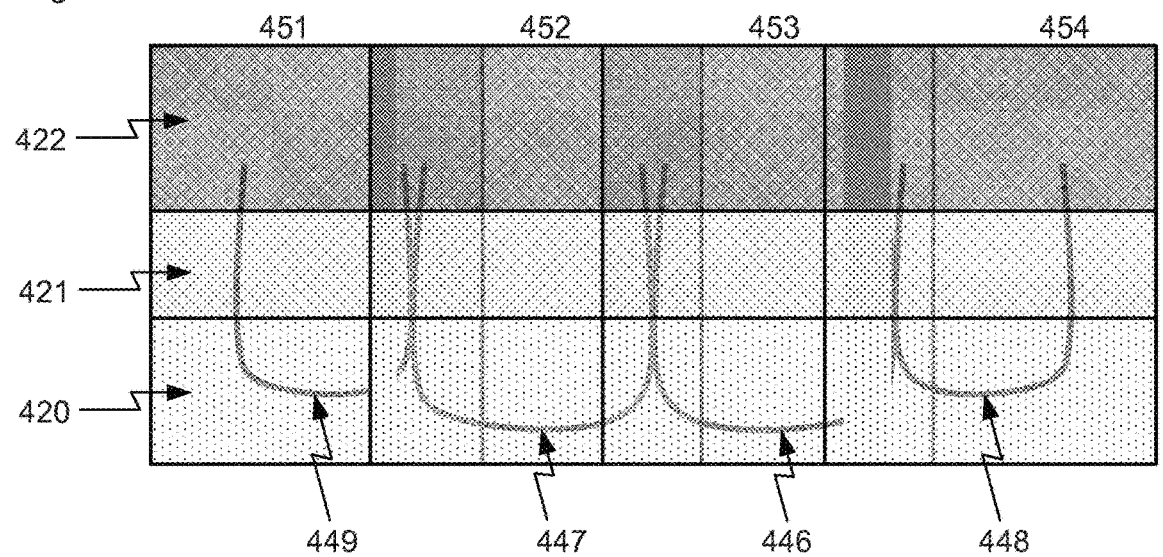

FIG. 4B shows a sketch of a simulated image created by superimposing the digital representations of the first and second milling blocks on the first and second digital restoration designs for each of the two left-right sets of digital restoration designs such that the digital restoration designs 446, 447, 448, 449 for the two left-right sets of dental restorations and the digital representations 451, 452, 453, 454 of four identical multi-shaded milling blocks are seen in the Figure. The digital representations of the multi-shaded milling blocks each have three layers 420, 421, 422 of material with different shades, where layer 420 have the brightest shade and layer 422 the darkest. Before starting to determine the preferred relative arrangements the digital representations of the multi-shaded milling blocks can be arranged such that the digital representations of all four multi-shaded milling blocks are aligned, but any other initial arrangement may evidently be used.

Figure 4C:
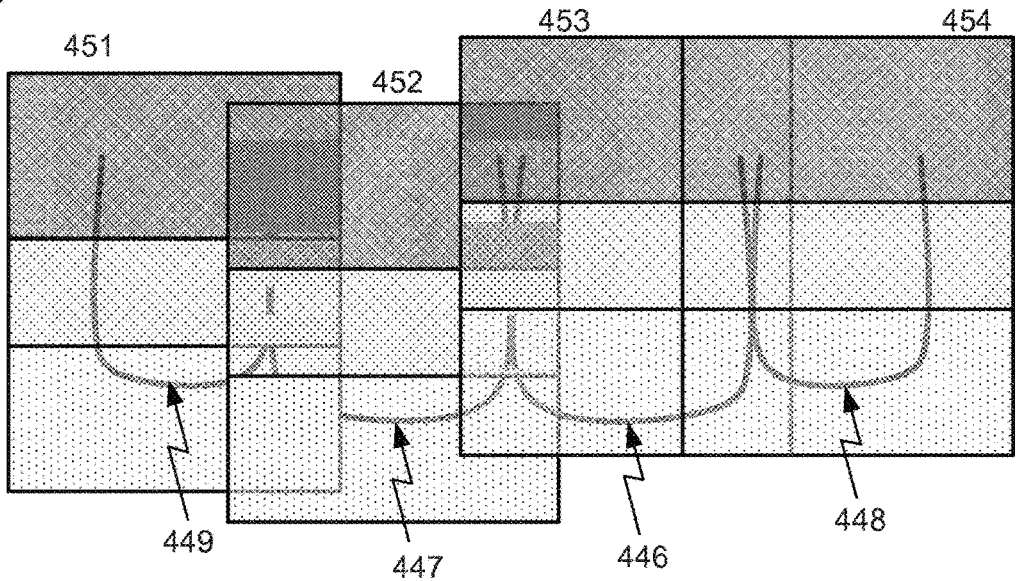

For each left-right set of dental restorations, the preferred first relative arrangement is determined by adjusting the relative arrangement of the digital representation of the first multi-shaded milling block and the first digital restoration design while inspecting the simulated image until the operator based on his or hers experience foresee that the manufactured dental restoration will have a satisfactory aesthetic appearance. FIG. 4C shows a case where the preferred first relative arrangements are determined by moving the digital representations of the first milling blocks 451, 452 downwards such that the height of the portions of the dental restoration which has the brightness of the brightest layer 420 is reduced for both restorations. In the illustrated preferred first relative arrangements the incisal edges of the right central incisor 447 and the right lateral incisor 449 have portions of the brightest shade which are of equivalent height.

Figure 4D:
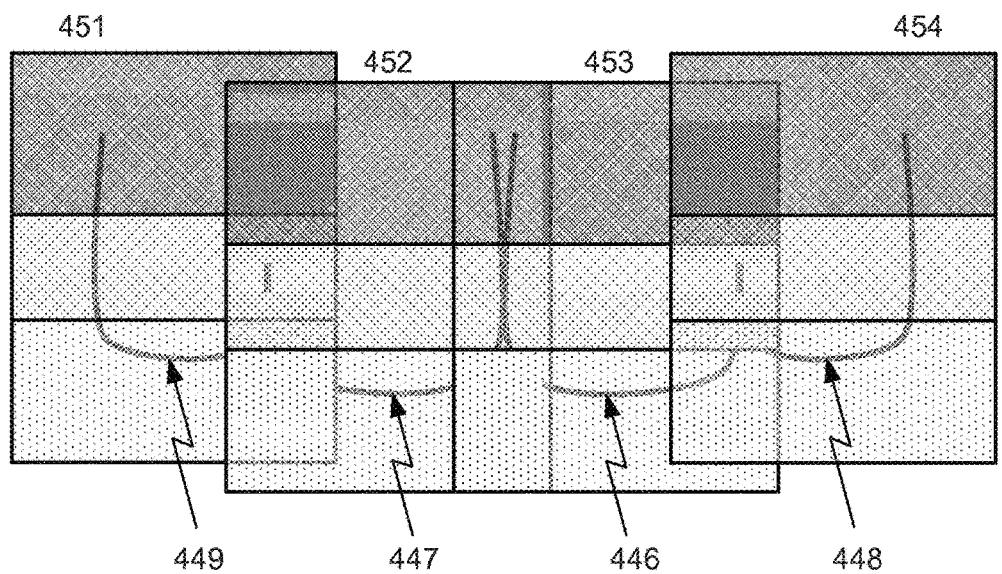

In FIG. 4D the preferred second relative arrangements of the two left-right sets are determined by aligning the digital representations of the multi-shaded milling blocks in each set. I.e. the digital representation 453 of the multi-shaded milling block for the upper left central incisor 446 is aligned with that 452 for the upper right central incisor 447, while the digital representation 454 of the multi-shaded milling block for the upper left lateral incisor 448 is aligned with that 451 for the upper right lateral incisor 449.

The aligning of the digital representations of the multi-shaded milling blocks for a left-right set of dental restorations can be seen as an example of determining the preferred second relative arrangement by mirroring the preferred first relative arrangement to the preferred second relative arrangement.

Figure 4E:
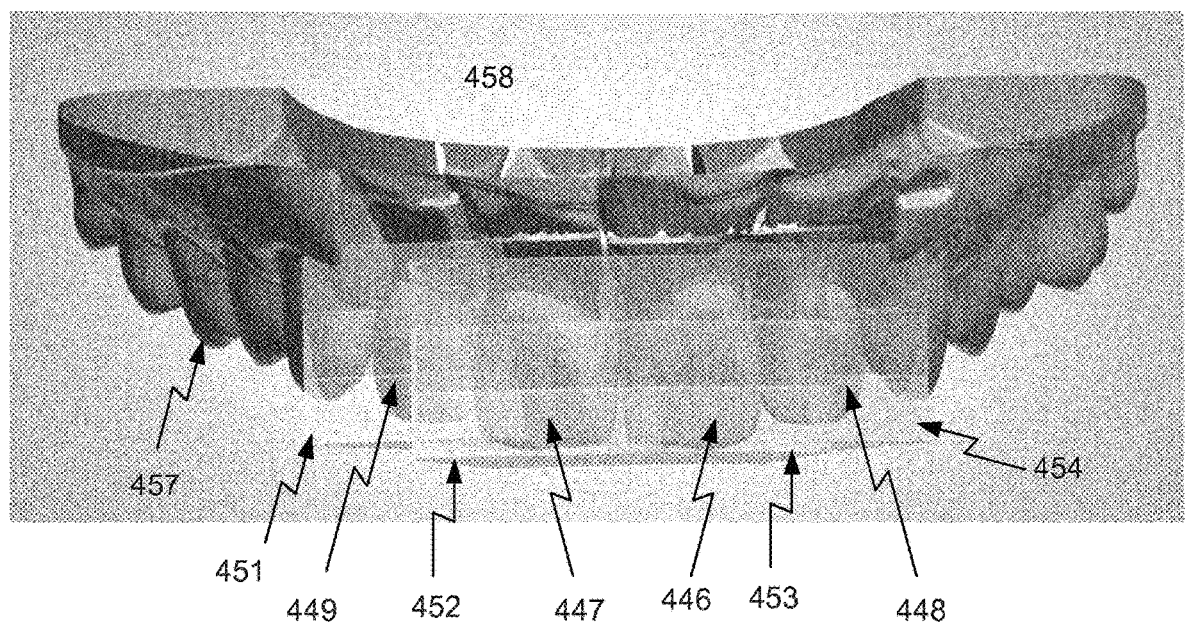

In a user interface for the computer program product according to the present invention, digital representations of the first and second multi-shaded milling blocks can be visualized in a simulated image as superimposed on the first and second digital restoration designs. FIG. 4E shows a section of a screen shot of a user interface according to the invention where simulated image comprises digital representations of milling blocks 451, 452, 453, 454, the four digital restoration designs 446, 447, 448, 449, and a digital 3D representation of the patient's existing teeth 457. When the operator has determined the preferred first relative arrangement, the digital representation of the second multi-shaded milling block 453 is aligned with that of the first multi-shaded milling block 452 by activating a virtual tool of said user interface (not included in the figure for simplicity). In the illustrated example, the digital representation 453 of the milling block for the upper left central incisor 446 has been aligned with the digital representation 452 of the milling block for the upper right central incisor 447, and the digital representation 454 of the milling blocks for the upper left lateral incisor 448 has been aligned with the digital representation 451 of the milling block for the upper right lateral incisor 449.

The digital restoration designs and the digital representations of the multi-shaded milling blocks schematically illustrated in FIGS. 4A-4D are all shown in 2D, but it is understood that the figures represent three dimensional structures such as those seen in FIG. 4E.

FIG. 5 shows an embodiment where the preferred first relative arrangement is determined from a simulated image created by mapping shade data of the digital representation of the first multi-shaded milling block onto the first digital restoration design.

Figure 5A:
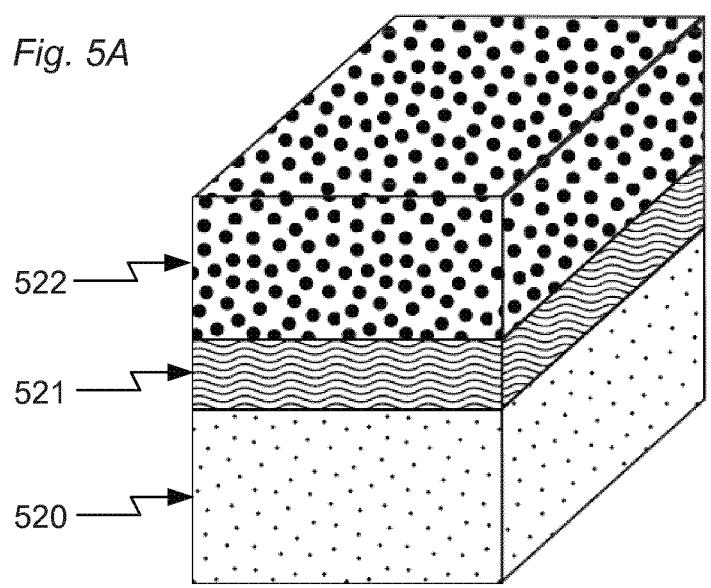
FIGS. 5A-5D show a schematic presentation of an embodiment.

In FIG. 5A is seen a 3D schematic illustration of a multi-shaded milling block having three layers of different shades where the shade of the middle layer 521 is brighter than that of the upper layer 522 and darker than that of the lower layer 520.

Figure 5B:
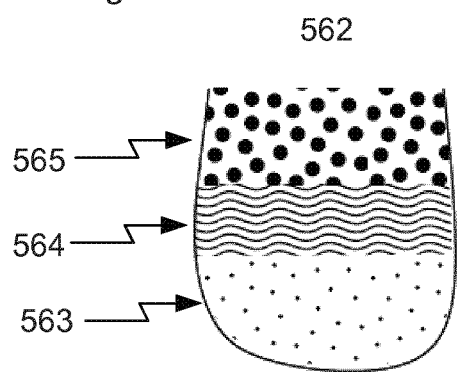

FIG. 5B shows a simulated image 562 created by mapping shade data of the digital representation of the first multi-shaded milling block onto the first digital restoration design based on a current relative arrangement of the two. The simulated image visualizes the shape and shade profile of a dental restoration manufactured based on the current relative arrangement. The region 563 of the simulated image near the incisal edge is shaded according to the shade of the lower layer 520, the middle region 564 is shaded according to the middle layer 521, and the upper region 565 is shaded according to the upper layer 522 of the multi-shaded milling block. The upper region of the simulated image corresponds to the portion of the manufactured dental restoration which is closest to the gingiva.

Figure 5C:
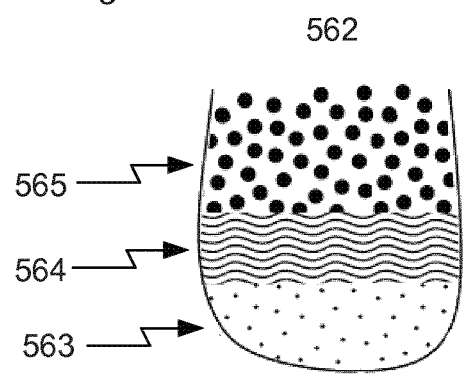

The relative arrangement of the digital representation of the first multi-shaded milling block and the first digital restoration design can be adjusted such the sub-volume of the multi-shaded milling block from which the dental restoration is formed is adjusted. Depending on the change in orientation and/or position of the first digital restoration design relative to the digital representation of the first multi-shaded milling block, the expected shade profile of the manufactured dental restoration changes and this is visualized by the simulated image. In FIG. 5C the first digital restoration design has been moved upwards relative to the digital representation of the first multi-shaded milling block such that the region 563 of the simulated image near its incisal edge is reduced compared to its size in the relative arrangement of FIG. 5B. Further the middle region 564 is displaced towards the incisal edge, and the size of the upper region 565 is increased. The relative position and orientation of the first digital restoration design can be adjusted using e.g. a computer mouse to move the first digital restoration design and the digital representation of the first multi-shaded milling block relative to each other. When the operator is satisfied with the look of the simulated image the preferred first relative arrangement has been determined.

Figure 5D:
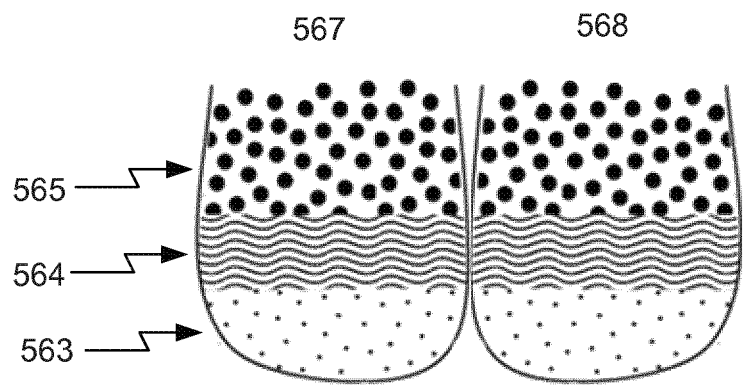

The preferred second relative arrangement can then be determined by e.g. mirroring the preferred first relative arrangement, such that the shade profiles of the manufactured first 567 and second 568 dental restorations are mirror symmetric as illustrated in FIG. 5D.

Figure 6:
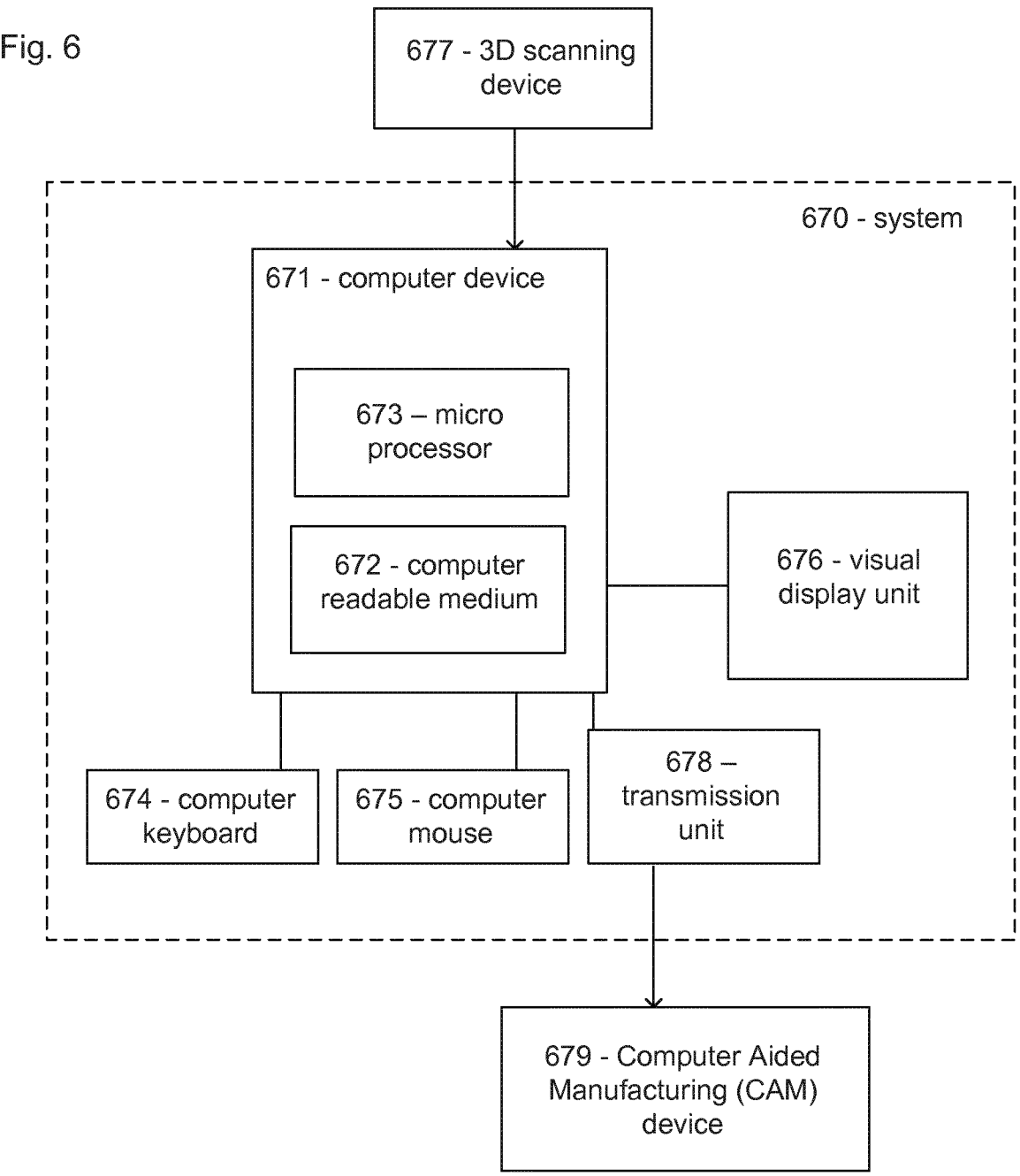
FIG. 6 shows a schematic of a system according to an embodiment of the present invention.

FIG. 6 shows a schematic of a system according to an embodiment of the invention. The system 670 comprises a computer device 671 comprising a computer readable medium 672 and a microprocessor 673. The system further comprises a visual display unit 676, a computer keyboard 674 and a computer mouse 675 for entering data and activating virtual buttons visualized on the visual display unit 676. The visual display unit 676 can be a computer screen.

The computer device 671 is capable of obtaining digital representations of at least a first and a second multi-shaded milling block, where each digital representation comprises shade data describing the shade distribution of the multi-shaded milling block. It is also capable of obtaining at least a first and a second digital restoration design based on which multi-shaded first and second dental restorations can be manufactured from the first and second multi-shaded milling blocks. The obtained digital representations and digital restoration designs can be stored in the computer readable medium 672 and provided to the processor 673. The system 670 is configured for allowing an operator to determine a preferred first relative arrangement of the first digital restoration design and the digital representation of the first multi-shaded milling block. This can be realized by creating a simulated image e.g. by mapping shade data of the digital representation of the first multi-shaded milling block onto the first digital restoration design based on a current relative arrangement of the two. The simulated image is then displayed in a user interface depicted on the visual display unit 676 and the operator can adjust the relative arrangement of the digital representation of the first multi-shaded milling block and the first digital restoration design using e.g. the computer mouse 675 or the computer keyboard 674 while observing the resulting changes in the simulated image on the visual display unit 676. The computer device 671 is configured for determining the preferred second relative arrangement of the second digital restoration design and the digital representation of the second multi-shaded milling block based on the preferred first relative arrangement, where the determining at least partly is performed by the microprocessor.

The computer device 671 is further capable of receiving a digital 3D representation of the patient's set of teeth from a 3D scanning device 677, such as the TRIOS intra-oral scanner manufactured by 3shape TRIOS A/S, or capable of receiving scan data from such a 3D scanning device and forming a digital 3D representation of the patient's set of teeth based on such scan data. The received or formed digital 3D representation can be stored in the computer readable medium 672 and provided to the microprocessor 673.

In determining the preferred first and second relative arrangements, one or more options can be presented to the operator, such as whether to copy of mirror the preferred first relative arrangement to the preferred second relative arrangement. The options can be presented in a user interface visualized on the visual display unit 676.

The system comprises a unit 678 for transmitting the digital restoration designs, and information about the multi-shaded milling blocks and the preferred first and second relative arrangements to e.g. a computer aided manufacturing (CAM) device 679 for manufacturing the dental restorations or to another computer system e.g. located at a milling center where the dental restorations are manufactured. The unit for transmitting can be a wired or a wireless connection.

The 3D scanning of the patient's set of teeth using the 3D scanning device 677 can be performed at a dentist while the designing of the dental restoration is performed at a dental laboratory. In such cases the digital 3D representation of the patient's set of teeth can be provided via an internet connection between the dentist and the dental laboratory.

Figure 7:
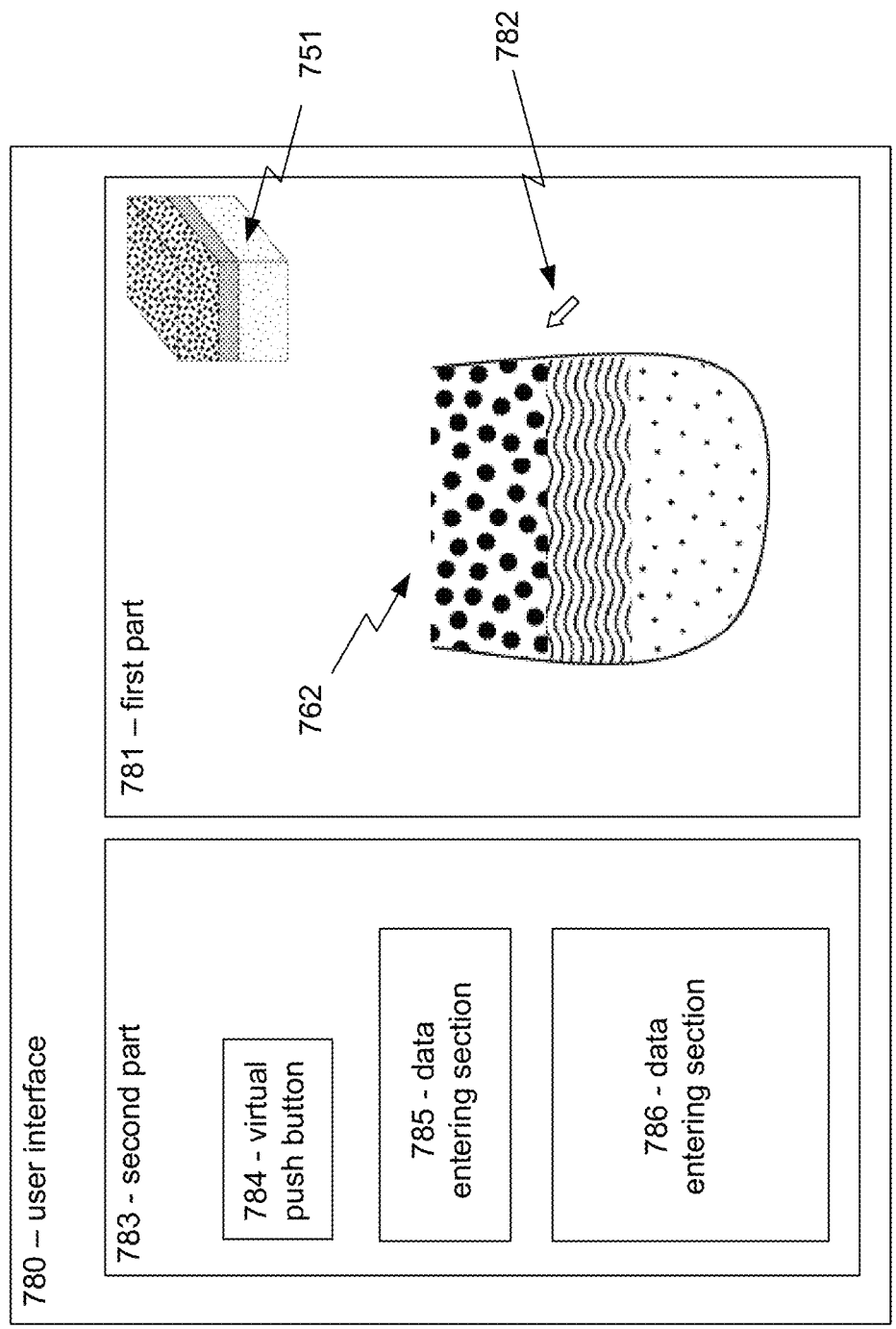
FIG. 7 shows a schematic of a user interface according to an embodiment of the invention.

FIG. 7 shows a schematic of a user interface according to an embodiment of the invention.

FIG. 7 shows a schematic of a user interface 780 comprising a first part 781 and a second part 783. In the first part a simulated image 762 is visualized together with a digital representation 751 of a first multi-shaded milling block.

The simulated image 762 is created by mapping shade data of the digital representation of the first multi-shaded milling block onto the first digital restoration design based on a current relative arrangement of the two.

The relative arrangement of the digital representation of the multi-shaded milling block and the first digital restoration design can be adjusted using a virtual movement tool 782. The virtual movement tool can be configured for grabbing the simulated image and moving it in the user interface using e.g. a computer mouse. The movement is then interpreted as a movement of the first digital restoration design only while the position and orientation of the digital representation of the multi-shaded milling block is assumed to be fixed. Computer implemented algorithms can then translate the corresponding change in the relative arrangement of the first digital restoration design and the digital representation of the first multi-shaded milling block into a change in the simulated image and the corresponding change in the expected shade profiled of a dental restoration manufactured from the multi-shaded milling block based on the current relative arrangement.

The second part 783 of the user interface comprises data entering sections 785, 786 for entering data relating to e.g. which type of milling block the dental restoration is to be manufactured from, and whether the preferred second relative arrangement is to be determined by e.g. copying or mirroring the preferred first relative arrangement.

A virtual push button 784 is configured for determining the preferred second relative arrangement from the preferred first relative arrangement taking into account the data entered in the data entering sections.

The user interface can be visualized on a visual display unit, such as a computer screen being part of a system configured for implementing the method according to the present invention.

FIG. 8 shows a schematic presentation of an embodiment where the preferred second relative arrangement is determined based on the relative arrangement of the incisal edge/occlusal surface of the first digital restoration design and the opposing surface of the digital representation of the first multi-shaded milling block.

Figure 8A:
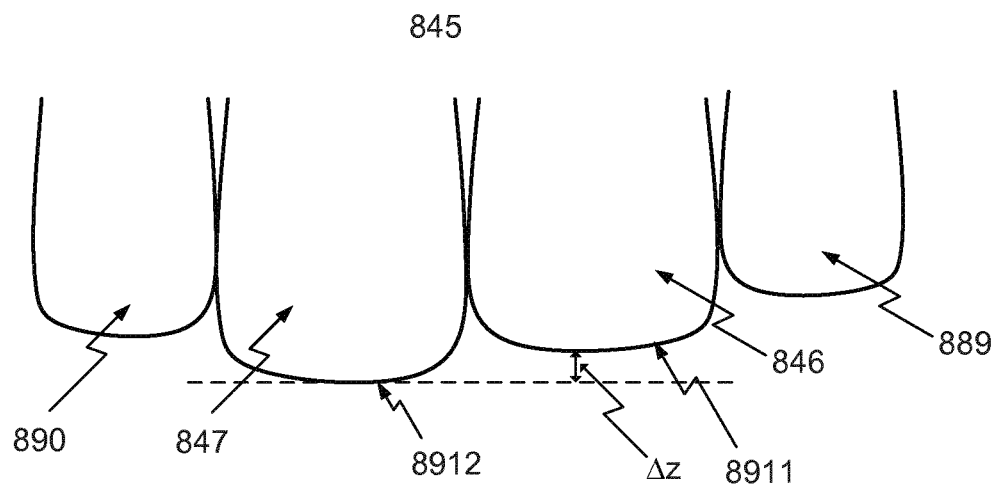
FIGS. 8A-8D show a schematic presentation of an embodiment.

FIG. 8A shows a schematic 845 of a left-right set of digital restoration designs 846, 847 for the left and right upper central incisors and a part of a digital representation of the patient's existing teeth showing the left and right upper lateral incisors 889, 890. The schematic shows the digital restoration designs and teeth as viewed by the operator such that e.g. the digital restoration design 846 for the patient's left central incisor appears on the right side of the schematic.

The first digital restoration design 847 and the second digital restoration design 846 are arranged according to the planned relative placement of the manufactured dental restorations when these are seated in the patient's mouth. The existing upper lateral incisors are asymmetric with the right lateral incisor 890 dropping below the left lateral incisor 889. In order to compensate for this the digital restoration designs 846, 847 are designed such that the incisal edge 8912 of the right upper central incisor 847 drops a length $\Delta z$ below the incisal edge 8911 of the left upper central incisor 846.

Figure 8B:
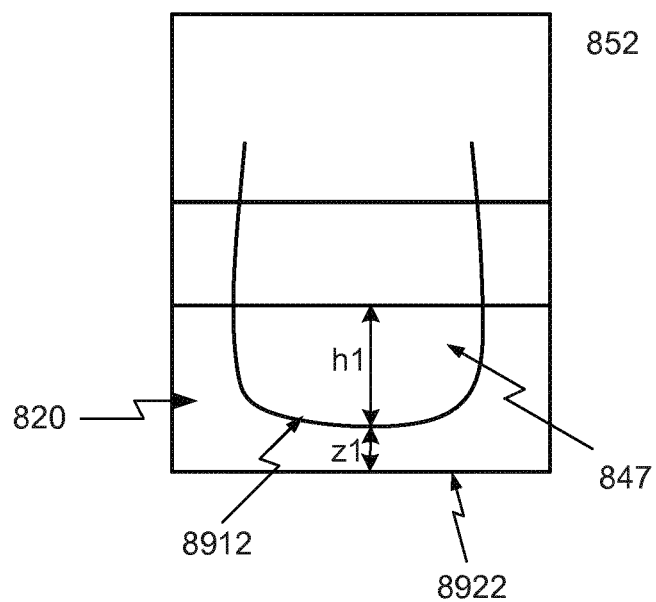

The preferred first relative arrangement is determined by adjusting the relative arrangement of the digital representation of the first multi-shaded milling block 852 and the first digital restoration design 847. This can be based on e.g. inspecting a simulated image until the operator based on his or hers experience foresee that the manufactured dental restoration will have a satisfactory aesthetic appearance. In the preferred first relative arrangement, the part of the dental restoration which has the shade of the lower layer 820 of the multi-shaded milling block has the height h1 as measured from the incisal edge 8912 as illustrated in FIG. 8B. The distance from the incisal edge 8912 of the first digital restoration design 846 and the opposing surface 8922 of the digital representation of the first multi-shaded milling block 852 is z1.

Figure 8C:
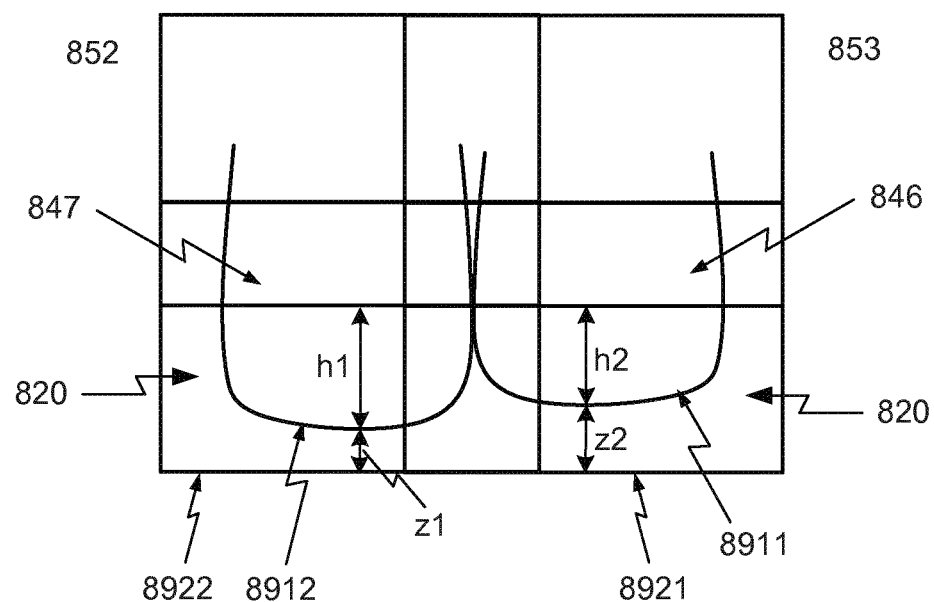
Figure 8D:
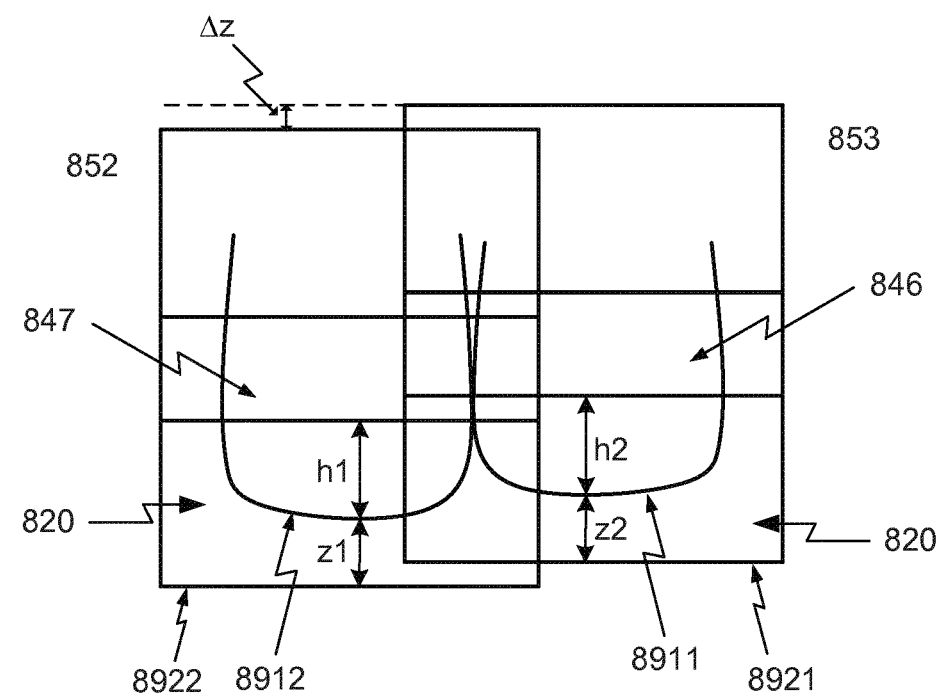

In some cases the dentist or dental technician decides that the even though the first and second digital restoration designs 846, 847 are designed to have the offset $\Delta z$ between their incisal edges 8911, 8912 the first and second dental restorations shall still be manufactured to have similar shade profiles at their incisal edges. This can be accomplished by mirroring the preferred first relative arrangement and further providing an offset $\Delta z$ to the digital representation of the second multi-shaded milling block 853. This process is illustrated in FIGS. 8C and 8D where FIG. 8C shows the result of mirroring the preferred first relative arrangement. After the mirroring, the part of the second digital restoration design 846 which has the shade of the lower layer 820 of the second multi-shaded milling block 853 has the height h2, and the distance from the incisal edge 8911 to the opposing surface 8921 of the digital representation of the second multi-shaded milling block 853 is z2, where h2 differs from h1. An offset of Δz is then provided to the digital representation of the second multi-shaded milling block 853 relative to the second digital restoration design 846 and/or relative to the digital representation of the first multi-shaded milling block 852 such that the distance z2 becomes identical to the distance z1. The incisal edge 8911 of the second digital restoration design 846 and the opposing surface 8921 of the digital representation of the second multi-shaded milling block 853 are then arranged relative to each other according to the relative arrangement of the incisal edge 8912 of the first digital restoration design 847 and the opposing surface 8922 of the digital representation of the first multi-shaded milling block 852. This provides that the height h2 of the incisal region of the second digital restoration design 846 increases to become is identical to the equivalent height h1 for the first dental restoration 847 and the determined preferred second relative arrangement is such that the manufactured first and second dental restorations have similar shade profiles at their incisal edges.

The dentist/operator can also decide that the height h2 of the incisal region of the second digital restoration design 846 is increased to a value which is below h1 but still higher than h2 without the offset if he finds that such a height provides a better overall aesthetics of the patient's set of teeth. The offset can e.g. be tuned by adjusting its value in a data entering section of a user interface according to the invention.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on an electronic data processing device or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for determining a relative arrangement of digital restoration designs and digital representations of multi-shaded milling blocks for use when designing a left-right set of digital restoration designs from multi-shaded milling blocks for manufacturing restorations based on the digital restoration designs, the method comprising:

obtaining digital representations of a first and a second multi-shaded milling block, where each digital representation comprises shade data describing the shade distribution of the multi-shaded milling block, wherein the digital representations of the first and second multi-shaded milling blocks are identical and represent identical multi-shaded milling blocks;

obtaining a left and a right digital restoration design of the left-right set of dental restorations;

determining a first relative arrangement of one of the left or the right digital restoration designs with respect to the digital representation of the first multi-shaded milling block and combining the one digital restoration design with the digital representation of the first milling block in order to obtain a shade profile of a first dental restoration to be manufactured; and determining a second relative arrangement of another of the left or the right digital restoration designs with respect to the digital representation of the second multi-shaded milling block by mirroring or copying the shade profile of the first relative arrangement in order to obtain a shade profile of a second dental restoration to be manufactured;

where determining the second relative arrangement comprises aligning a position of the digital representation of the second multi-shaded milling block with a position of the digital representation of the first multi-shaded milling block.

2. The method according to claim 1, wherein determining the second relative arrangement comprises copying the first relative arrangement to the second relative arrangement.

3. The method according to claim 1, wherein determining the first relative arrangement comprises adjusting the relative arrangement of the left digital restoration design and the digital representation of the first multi-shaded milling block while inspecting a simulated image.

4. The method according to claim 3, wherein the simulated image at least partly created by mapping the shade data of the digital representation of the first multi-shaded milling block onto the left digital restoration design.

5. The method according to claim 3, wherein the simulated image is at least partly created by superimposing the digital representations of the first and second milling blocks on the left and right digital restoration designs.

6. The method according to claim 1, wherein the digital representations of the first and second multi-shaded milling blocks comprise both shade data describing the shade distribution and shape data describing the shape of the multi-shaded milling block.

7. The method according to claim 1, wherein aligning the digital representation of the second multi-shaded milling block with the digital representation of the first multi-shaded milling block is based on the shade data of the digital representations.

8. The method according to claim 1, wherein aligning the digital representation of the second multi-shaded milling block with the digital representation of the first multi-shaded milling block is based on shape data of the digital representations.

9. The method according to claim 1, wherein one of the digital representations of the first and second multi-shaded milling blocks relate to a left geometry multi-shaded milling block while the other relates to a right geometry multi-shaded milling block.

10. The method according to claim 1, wherein the shade distributions of the multi-shaded milling blocks comprise a number of layers of different shades, and where the shade data of the digital representations of the multi-shaded milling blocks comprises corresponding virtual layers.

11. The method according to claim 1, wherein the second relative arrangement is determined after the first relative arrangement.

12. The method according to claim 1, wherein the second relative arrangement is determined from the relative arrangement of the incisal edge/occlusal surface of the left digital restoration design and the opposing surface of the digital representation of the first multi-shaded milling block in the first relative arrangement.

13. The method according to claim 1, wherein determining the second relative arrangement comprises providing an offset to the digital representation of the second multi-shaded milling block relative to the digital representation of the first multi-shaded milling block and/or relative to the left digital restoration design.

14. The method according to claim 1, where determining the second relative arrangement at least partly is performed by computer implemented algorithms executed by an electronic data processing device.

15. The method according to claim 1, wherein at least one of the digital representations of the multi-shaded milling blocks is a digital 3D representation describing the 3D shape and shade distribution of another of the milling blocks.

16. The method according to claim 1, wherein determining the first relative arrangement of the left digital restoration design and the digital representation of the first multi-shaded milling block includes adjusting a relative arrangement of the left digital restoration design and the digital representation of the first milling block.

17. The method according to claim 1, wherein determining the second relative arrangement comprises mirroring the first relative arrangement to the second relative arrangement.

18. The method according to claim 1, wherein aligning the digital representation of the second multi-shaded milling block with the digital representation of the first multi-shaded milling block is based on an edge or surface of the digital representations of the milling blocks.

19. A user interface for determining a relative arrangement of digital restoration designs and digital representations of multi-shaded milling blocks for use when manufacturing a left-right set of dental restorations from multi-shaded milling blocks, where the user interface is configured for:
  obtaining digital representations of a first and a second multi-shaded milling block, where each digital representation comprises shade data describing the shade distribution of the multi-shaded milling block, wherein the digital representations of the first and second multi-shaded milling blocks are identical and represent identical multi-shaded milling blocks;
  obtaining a left and a right digital restoration design of the left-right set of dental restorations;
  visualizing at least the left digital restoration design and at least the shade data of the digital representation of the first multi-shaded milling block;
  determining a first relative arrangement of one of the left or the right digital restoration designs with respect to the digital representation of the first multi-shaded milling block and combining the one digital restoration design with the digital representation of the first milling block in order to obtain a shade profile of a first dental restoration to be manufactured; and
  determining a second relative arrangement of another of the left or the right digital restoration designs with respect to the digital representation of the second multi-shaded milling block by mirroring the shade profile of the first relative arrangement in order to obtain a shade profile of a second dental restoration to be manufactured;
  where determining the second relative arrangement comprises aligning a position of the digital representation of the second multi-shaded milling block with a position of the digital representation of the first multi-shaded milling block.

20. The user interface according to claim 19, wherein aligning the digital representation of the second multi-shaded milling block with the digital representation of the first multi-shaded milling block is based on an edge or a surface of the multi-shaded milling blocks.

21. The user interface according to claim 19, wherein determining the first relative arrangement of the left digital restoration design and the digital representation of the first multi-shaded milling block includes adjusting a relative arrangement of the left digital restoration design and the digital representation of the first milling block.

22. A method for determining a relative arrangement of digital restoration designs and digital representations of multi-shaded milling blocks for use when manufacturing a left-right set of dental restorations from multi-shaded milling blocks, the method comprising:
  obtaining digital representations of a first multi-shaded milling block and a second multi-shaded milling block, where each digital representation comprises shade data describing the shade distribution of the multi-shaded milling block, wherein the digital representations of the first and second multi-shaded milling blocks are identical and represent identical multi-shaded milling blocks;
  obtaining a left and a right digital restoration design of the left-right set of dental restorations;
  visualizing at least the left digital restoration design and at least the shade data of the digital representation of the first multi-shaded milling block;
  determining a first relative arrangement of one of the left or the right digital restoration designs with respect to the digital representation of the first multi-shaded milling block and combining the one digital restoration design with the digital representation of the first milling block in order to obtain a shade profile of a first dental restoration to be manufactured;
  determining a second relative arrangement of another of the left or the right digital restoration designs with respect to the digital representation of the second multi-shaded milling block by mirroring the shade profile of the first relative arrangement in order to obtain a shade profile of a second dental restoration to be manufactured;
  where determining the second relative arrangement comprises aligning a position of the digital representation of the second multi-shaded milling block with a position of the digital representation of the first multi-shaded milling block; and
  wherein aligning the digital representation of the second multi-shaded milling block with the digital representation of the first multi-shaded milling block is based on an edge or a surface of the multi-shaded milling blocks.

* * * * *